(12) United States Patent
Hegyi et al.

(10) Patent No.: US 9,677,916 B2
(45) Date of Patent: Jun. 13, 2017

(54) ENERGY SYSTEM MONITORING

(71) Applicant: Palo Alto Research Center Incorporated, Palo Alto, CA (US)

(72) Inventors: Alex Hegyi, San Francisco, CA (US); Peter Kiesel, Palo Alto, CA (US); Ajay Raghavan, Mountain View, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 359 days.

(21) Appl. No.: 14/331,318

(22) Filed: Jul. 15, 2014

(65) Prior Publication Data

US 2016/0018319 A1 Jan. 21, 2016

(51) Int. Cl.
| | | |
|---|---|---|
| *G01D 5/353* | (2006.01) | |
| *G01R 31/36* | (2006.01) | |
| *G01L 1/24* | (2006.01) | |
| *G02B 6/12* | (2006.01) | |
| *G02B 6/293* | (2006.01) | |

(52) U.S. Cl.
CPC ....... *G01D 5/35383* (2013.01); *G01D 5/3539* (2013.01); *G01D 5/35316* (2013.01); *G01L 1/246* (2013.01); *G01R 31/3606* (2013.01); *G02B 6/12009* (2013.01); *G02B 6/2938* (2013.01); *G01N 2201/088* (2013.01)

(58) Field of Classification Search
CPC . G01L 1/246; G01R 31/3606; G01R 31/3627; G01R 31/3634; G01R 31/3641; G01R 31/3679; H01M 10/48; H01M 10/486; H01M 10/4285; H01M 10/4278; H01M 2010/4271; H01M 8/04067; G01D 5/35316; G01D 5/35383; G01D 5/3539; G01D 5/3537; G01D 5/35374; G01D 5/357387; G01D 5/35396; G01K 11/32; G01M 11/083; G01N 2201/088; G02B 6/12009; G02B 6/2938
See application file for complete search history.

(56) References Cited

U.S. PATENT DOCUMENTS

| | | |
|---|---|---|
| 4,240,747 A | 12/1980 | Harmer |
| 5,660,944 A | 8/1997 | Sprengel et al. |
| 5,949,219 A | 9/1999 | Weiss |

(Continued)

FOREIGN PATENT DOCUMENTS

| | | |
|---|---|---|
| EP | 1 324 516 A2 * | 7/2003 |
| EP | 2492989 | 10/2013 |

(Continued)

OTHER PUBLICATIONS

File History for U.S. Appl. No. 13/630,660.

(Continued)

*Primary Examiner* — Gordon J Stock, Jr.
(74) *Attorney, Agent, or Firm* — Hollingsworth Davis, LLC

(57) ABSTRACT

An optical coupler includes at least one input waveguide and a plurality of output waveguides. The optical coupler spatially disperses optical signals carried on the input waveguide according to wavelength to the output waveguides. The input waveguides and the output waveguides are arranged to provide crosstalk between optical signals carried on the output waveguides.

37 Claims, 18 Drawing Sheets

(56) References Cited

U.S. PATENT DOCUMENTS

| | | |
|---|---|---|
| 5,995,686 A | 11/1999 | Hamburger et al. |
| 6,051,437 A | 4/2000 | Luo et al. |
| 6,265,100 B1 | 7/2001 | Saaski et al. |
| 6,285,807 B1 | 9/2001 | Walt et al. |
| 6,379,969 B1 | 4/2002 | Mauze et al. |
| 6,828,055 B2 | 12/2004 | Kearl |
| 7,135,342 B2 | 11/2006 | Colvin, Jr. et al. |
| 7,155,075 B2 | 12/2006 | Rajendran et al. |
| 7,263,246 B1 | 8/2007 | Duan et al. |
| 7,306,951 B1 | 12/2007 | Benson et al. |
| 7,310,153 B2 | 12/2007 | Kiesel et al. |
| 7,315,667 B2 | 1/2008 | Kiesel et al. |
| 7,433,552 B2 | 10/2008 | Kiesel |
| 7,511,823 B2 | 3/2009 | Schultz et al. |
| 7,522,786 B2 | 4/2009 | Kiesel et al. |
| 7,589,312 B2 | 9/2009 | Kojima |
| 7,695,970 B2 | 4/2010 | Parnas et al. |
| 7,701,590 B2 | 4/2010 | Kiesel et al. |
| 7,718,948 B2 | 5/2010 | Kiesel |
| 7,766,544 B2 | 8/2010 | Shibuya et al. |
| 8,097,352 B2 | 1/2012 | Fuse |
| 8,143,070 B2 | 3/2012 | Tokhtuev et al. |
| 8,148,165 B2 | 4/2012 | Nakano |
| 8,241,911 B2 | 8/2012 | Ascheman et al. |
| 8,268,493 B2 | 9/2012 | Cetegen et al. |
| 8,437,582 B2 | 5/2013 | Kiesel |
| 8,594,470 B2 | 11/2013 | Kiesel et al. |
| 8,729,862 B2 | 5/2014 | Yebka et al. |
| 8,808,890 B2 | 8/2014 | Fuse |
| 9,000,718 B2 | 4/2015 | Park |
| 2004/0033004 A1 | 2/2004 | Welch et al. |
| 2005/0026134 A1 | 2/2005 | Miller et al. |
| 2006/0045412 A1 | 3/2006 | Xiao et al. |
| 2008/0231836 A1 | 9/2008 | Curello et al. |
| 2009/0027009 A1 | 1/2009 | Sievertsen |
| 2009/0091759 A1* | 4/2009 | Pan .......................... G01J 3/02 356/418 |
| 2009/0220189 A1 | 9/2009 | Kiesel |
| 2009/0274849 A1 | 11/2009 | Scott et al. |
| 2010/0032009 A1 | 2/2010 | Skryabin |
| 2010/0247027 A1 | 9/2010 | Xia et al. |
| 2012/0232354 A1 | 9/2012 | Ecker et al. |
| 2012/0321242 A1 | 12/2012 | Schade et al. |
| 2013/0071739 A1 | 3/2013 | Tajima et al. |
| 2013/0312947 A1 | 11/2013 | Bandhauer et al. |
| 2013/0314094 A1 | 11/2013 | Farmer et al. |
| 2013/0316198 A1 | 11/2013 | Bandhauer et al. |
| 2014/0072836 A1 | 3/2014 | Mills |
| 2014/0092375 A1 | 4/2014 | Raghavan et al. |
| 2014/0203783 A1 | 7/2014 | Kiesel et al. |
| 2014/0272493 A1 | 9/2014 | Evans et al. |
| 2014/0312828 A1 | 10/2014 | Vo et al. |
| 2014/0363747 A1 | 12/2014 | Evans et al. |
| 2015/0214757 A1 | 7/2015 | Zane et al. |
| 2015/0255824 A1 | 9/2015 | Evans et al. |

FOREIGN PATENT DOCUMENTS

| | | |
|---|---|---|
| JP | 63301470 | 12/1988 |
| JP | 2009059582 | 3/2009 |
| WO | WO 2013/111698 A1 * | 8/2013 |
| WO | WO2014026093 | 2/2014 |

OTHER PUBLICATIONS

Cao-Paz et al., "A Multi-Point Sensor Based on Optical Fiber for the Measurement of Electrolyte Density in Lead-Acid Batteries", Sensors 2010, 10, pp. 2587-2608.

Corbellini et al., "Modified POF Sensor for Gaseous Hydrogen Fluoride Monitoring in the Presence of Ionizing Radiations", IEEE Transactions on Instrumentation and Measurement, vol. 61, No. 5, May 2012, pp. 1201-1208.

Grobnic et al., "Sapphire Fiber Bragg Grating Sensor Made Using Femtosecond Laser Radiation for Ultrahigh Temperature Applications", IEEE Photonics Technology Letters, vol. 16, No. 11, Nov. 2004, p. 2505-2507.

Haase, "Strain Sensors Based on Bragg Gratings", IMEKO $20^{th}$ TC3, $3^{rd}$ TC16 and $1^{st}$ TC22 International Conference Cultivating Metrological Knowledge, Nov. 27, 2007, 8 pages.

Jansen et al., "Low-Cost Flexible Packaging for High-Power Li-Ion HEV Batteries", FreedomCar & Vehicle Technologies Office, Jun. 2004, 56 pages.

Juergens et al., "Performance Evaluation of Fiber Bragg Gratings at Elevated Temperatures", NASA, Jan. 2004, 14 pages.

Kersey et al., "Fiber Grating Sensors", Journal of Lightwave Technology, vol. 15, No. 8, Aug. 1997, pp. 1442-1463.

Lee et al., "In Situ Monitoring of Temperature Inside Lithium-Ion Batteries by Flexible Micro Temperature Sensors", Sensors 2011, 11, pp. 9942-9950.

Liang et al., "Highly Sensitive Fiber Bragg Grating Refractive Index Sensors", Applied Physics Letters, vol. 86, 2005, pp. 151122-1-151122-3.

Merzbacher et al., "Fiber Optic Sensors in Concrete Structures: A Review", Smart Mater. Struct., 5, 1996, pp. 196-280.

Micron Optics, "Optical Fiber Sensors Guide", 21 pages.

Qi et al., "In Situ Observation of Strains During Lithiation of a Graphite Electrode", Journal of the Electrochemical Society, vol. 157 (6), 2010, pp. A741-A747.

Qin et al., "Specific Fluorescence Determination of Lithium Ion Based on 2-(2-hydroxyphenyl)benzoxazole", The Royal Society of Chemistry, 2001, pp. 1499-1501.

Rodrigues et al., "A Review of State-of-Charge Indication of Batteries by Means of A.C. Impedance Measurements", Journal of Power Sources, vol. 87, 2000, pp. 12-20.

Sang et al., "Temperature-Insensitive Chemical Sensor Based on a Fiber Bragg Grating", Sensors and Actuators B 120, 2007, pp. 754-757.

Mar. 7, 2012, Siegel et al., "Neutron Imaging of Lithium Concentration in FLP Pouch Cell Battery", Journal of the Electrochemical Society, 158 (6), 2011, 8 pages.

Tang et al., "Measurement of Chloride-Ion Concentration with Long-Period Grating Technology", Smart Mater. Struct. vol. 16, 2007, pp. 665-672.

Udd et al., "Fiber Optic Distributed Sensing Systems for harsh Aerospace Environments", 12 pages.

Van Steenkiste et al., "Strain and Temperature Measurement with Fiber Optic Sensors", 1997, 9 pages.

File History for U.S. Appl. No. 14/257,673.

Chehura et al. "Temperature and strain discrimination using a single tilted fibre Bragg grating", Opt. Commun., vol. 275, No. 2, Jul. 2007, pp. 344-347.

Guan et al. "Simultaneous strain and temperature measurement using a single fibre Bragg grating", Electron. Lett.,vol. 36, No. 12, 2000, pp. 1018-1019.

Jin et al. "Geometric representation of errors in measurements of strain and temperature", Opt. Eng., vol. 36, No. 8, 1997, pp. 2272-2278.

Jin et al. "Simultaneous measurement of strain and temperature: error analysis". Opt. Eng .• vol. 36, No. 2, 1997. pp. 598-609.

Klein et al., "Optimal Charging Strategies in Lithium-Ion Battery", 2011 American Control Conference, Jun. 29-Jul. 1, 2011, pp. 382-387.

Kumai et al., "Gas Generation Mechanism Due to Electrolyte Decomposition in Commercial Lithium-Ion Cell", Journal of Power Sources 81-82, 1999, pp. 715-719.

Patrick et al. "Hybrid fiber Bragg grating/long period fiber grating sensor for strain/temperature discrimination", IEEE Photonics Technol. Lett., vol. 8, No. 9, 1996, pp. 1223-1225.

Pinson et al., Theory of SEI Formation in Rechargeable Batteries: Capacity Fade, Accelerated Aging and Lifetime Prediction, $223^{rd}$ ECS Meeting, May 12-17, 2013, 29 pages.

Rao: "In-fibre Bragg grating sensors", Meas. Sci. Technol., vol. 8, No. 4, Apr. 1997, pp. 355-375.

(56) References Cited

OTHER PUBLICATIONS

Reimers et al. "Electrochemical and in Situ X-Ray Diffraction Studies of Lithium Intercalation in LixCo02", Journal of the Electrochemical Society, 139 (8),1992.
Roth et al., "Thermal Abuse Performance of 18650 Li-Ion Cells", Sandia Report, Mar. 2004, pp. 1-139.
U.S. Appl. No. 14,257,673, filed Apr. 21, 2014, Raghavan et al.
Saha et al. "Battery Data Set", NASA Ames Prognostics Data Repository, 2007, Available online: http://tLarc.nasa.gov/tech/dash/pcoe/prognostic-data-repository/.
Sethuraman et al. "Surface structural disordering in graphite upon lithium intercalation/deintercalation", Journal of Power Sources 195 (2010) 3655-3660.
Smith et al., "Power and Thermal Characterization of a Lithium-Ion Battery Pack for Hybrid-Electric Vehicles", Journal of Power Sources 160, 2006, pp. 662-673.
Triollet et al. "Discriminated measures of strain and temperature in metallic specimen with embedded superimposed long and short fibre Bragg gratings", Meas. Sci. Technol., vol. 22, No. 1, Jan. 2011, pp. 015202.
Wang et al., "Aging Effects to Solid Electrolyte Interface (SEI) Membrane Formation and the Performance Analysis of Lithium Ion Batteries", Int. J. Electrochem, Sci., 6, 2011, pp. 1014-1026.
Wang et al. "Simultaneous measurement of strain and temperature using dual-period fiber grating", Proc. SPIE, vol. 4579, 2001, pp. 265-268.
Wang et al. "Understanding Volume Change in Lithium-Ion Cells during Charging and Discharging Using In Situ Measurements", Journal of the Electrochemical Society, 154 (1), 2007.
Xu et al. "Discrimination between strain and temperature effects using dual-wavelength fibre grating sensors", Electron. Lett., vol. 30, No. 13, pp. 1085-1087, 1994.
Zhao et al. "Discrimination methods and demodulation techniques for fiber Bragg grating sensors", Opt. Lasers Eng., vol. 41, No. 1, pp. 1-18, Jan. 2004.
Zhou et al. "Simultaneous measurement for strain and temperature using fiber Bragg gratings and multimode fibers", Appl. Opt., vol. 47, No. 10, Apr. 2008, pp. 1668-1672.
File History for U.S. Appl. No. 14/242,853.
Koch et al., "Arrayed waveguide grating interrogator for fiber Bragg grating sensors: measurement and simulation", Applied Optics, vol. 51, No. 31, Nov. 1, 2012, pp. 7718-7723.
Niewczas et al. "Performance Analysis of the Fiber Bragg Grating Interrogation System Based on an Arrayed Waveguide Grating", IEEE Transactions on Instrumentation and Measurement, vol. 53, No. 4, Aug. 2004, pp. 1192-1195.
Li et al., "Preliminary Investigation of an SOI-based Arrayed Waveguide Grating Demodulation Intergration Microsystem" Scientific Reports, May 6, 2014, 6 pages.
File History for EP App. No. 15174916.5 as retrieved from the Ep Electronic File System on Aug. 5, 2016, 117 pages.

* cited by examiner

ENERGY SYSTEM MONITORING

STATEMENT REGARDING FEDERALLY SPONSORED RESEARCH AND DEVELOPMENT

This invention was made with government support under contract DE-AR0000274 awarded by ARPA-E (Advanced Research Projects Agency-Energy). The government has certain rights in the invention.

TECHNICAL FIELD

This application relates generally to techniques for monitoring and/or managing systems, including energy storage and/or power generation systems. The application also relates to components, devices, systems, and methods pertaining to such techniques.

BACKGROUND

Battery management systems that rely on external cell performance parameters to determine state-of-charge (SOC) and/or state-of-health (SOH) result in conservative overdesign to manage the uncertainty in battery state-of-charge and battery degradation with aging. This reliance on conservative overdesign of batteries has affected the widespread adoption of clean technologies such as electric vehicles and power grid storage. Conservative overdesign of batteries arises in part because the battery state cannot be fully understood from external parameters alone.

SUMMARY

Various embodiments described herein involve systems and methods for monitoring and/or managing systems, such as energy storage devices, power generation systems and other such devices and systems. Some embodiments involve an optical monitoring system that can be used to monitor an energy system. The monitoring system includes N>1 optical sensors. Each optical sensor emanates output light in response to input light, the output light having a centroid wavelength that changes in response to a sensed parameter. The output light of the optical sensors is optically coupled to the input waveguide and the optical coupler spatially disperses the light from the input waveguide according to wavelength. The output light emanating from each optical sensor is optically coupled through at least one output waveguide to a photodetector. The electrical signal generated by the photodetector in response to the sensor output light provides information about the sensed parameter.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DESCRIPTION

Embodiments described in this disclosure involve optically-based monitoring and management systems. Such systems may be particularly useful for monitoring and/or managing energy devices and/or systems that generate, store and/or distribute energy. The approaches disclosed herein enable comprehensive real-time performance monitoring and management of these systems, reducing the need for overdesign of energy systems. The monitoring systems of the present disclosure combine fiber optic sensors to sense internal and/or external parameters of the energy system. The sensed information may be used by smart algorithms to infer and/or predict energy system state and to provide feedback for energy system management. The approaches disclosed herein can be used to monitor and/or manage a variety of systems, but are particularly applicable to modularized systems such as batteries and battery packs, fuel cell stacks, turbine-based power systems, solar arrays, and other types of energy storage and power generation devices and systems. Some monitoring and/or management systems are described herein in the context of battery system monitoring, although it will be appreciated that the disclosed approaches are applicable to monitoring and/or management for any type of system.

Figure 1:
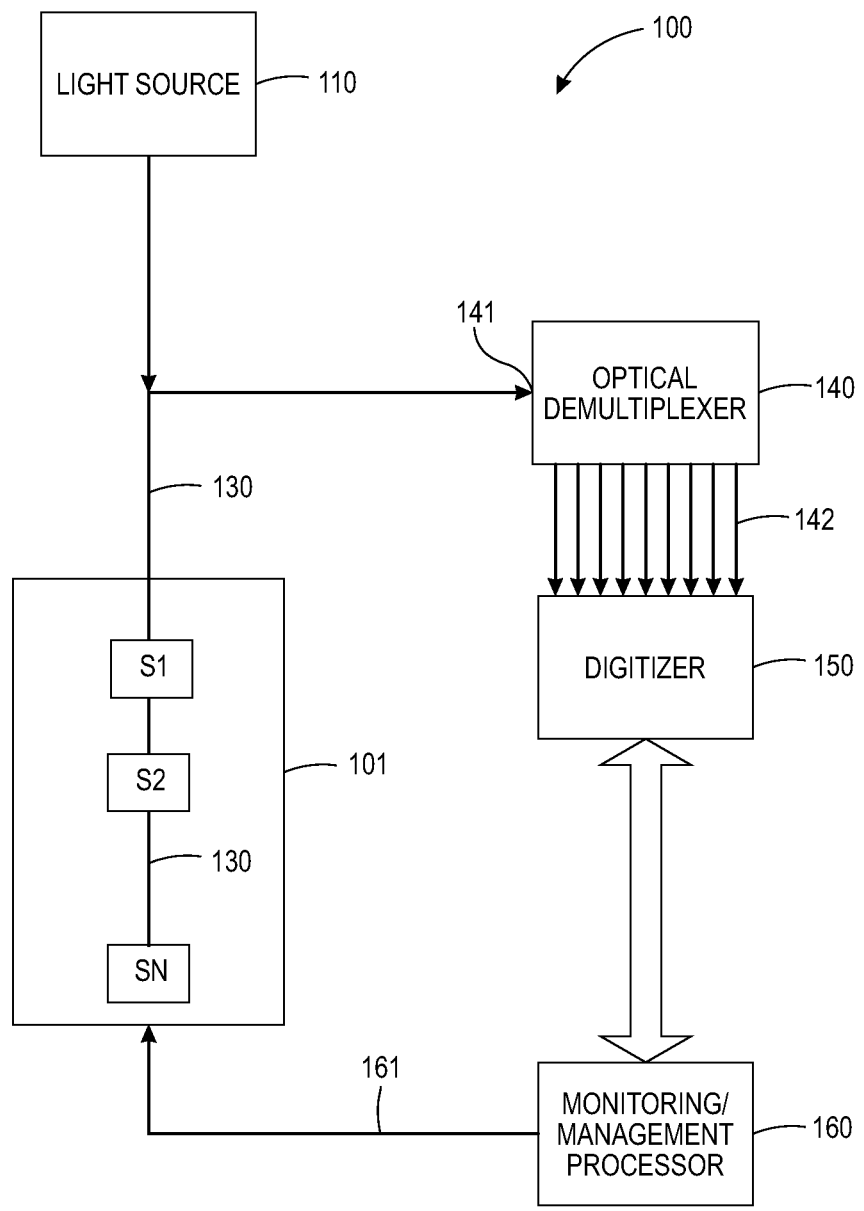
FIG. 1 shows a general block diagram of a monitoring and management system that includes optical demultiplexing according to embodiments described herein.

Some embodiments are directed to monitoring systems that involve optical sensing with wavelength domain demultiplexing. FIG. 1 is a block diagram of a monitoring and management system (MMS) 100. Multiple internal optical sensors, S1, S2, . . . SN, are arranged to sense multiple internal properties of the battery 101. For example, at least some of the optical sensors S1, S2, . . . SN may be disposed within the battery 101 and configured to measure one or more internal battery parameters such as internal temperature, stress, strain, acoustic emission, ion concentration, chemistry, presence and/or concentration of gas, and/or other internal parameters of the battery 101. In some embodiments, sensors S1, S2, . . . SN are each configured to sense the same parameter. In other embodiments, one or more of the sensors S1, S2, . . . SN are configured to sense a parameter that is different from a parameter sensed by another sensor. In some embodiments, the outputs of multiple sensors that sense the same parameter may be combined to yield an average or composite value for the sensed parameter. In some embodiments, multiple sensors that sense the same parameter can be used to develop a map of the spatial distribution of the parameter in the interior and/or at the exterior of the battery 101.

As illustrated by FIG. 1, optical sensors S1, S2, . . . SN are disposed on one or more sensor waveguides (shown in FIG. 1 as a single fiber optic (FO) cable 130) and are embedded within a battery 101. Each of the sensors S1, S2, . . . SN may operate within a different wavelength band from other sensors on the FO cable 130. For example, sensor S1 may operate within a first wavelength band centered at wavelength $\lambda_1$, sensor S2 may operate within a second wavelength band centered at $\lambda_2$, and sensor SN may operate within an Nth wavelength band centered at $\lambda_N$. Each wavelength band $\lambda_1, \lambda_2, \ldots \lambda_N$ may be selected so that it does not substantially overlap with the wavelength bands of the other sensors. The optical sensors S1, S2, . . . SN are optically coupled to a light source 110, which may be a broadband light source that supplies excitation light across a broad wavelength band that spans the operating wavelength bands of the optical sensors S1, S2, . . . SN. Output light from optical sensors S1, S2, . . . SN is carried on sensor waveguide fiber optic cable 130 to an input waveguide 141 of an optical coupler 140. The optical coupler 140 is a wavelength domain optical demultiplexer that spatially disperses light from the input waveguide 141 to multiple output waveguides 142 according to the wavelength of the light. In various implementations, the optical coupler may comprise a linear variable transmission structure and/or an arrayed waveguide grating, for example.

The output waveguides 142 are optically coupled to a digitizer 150 that may include multiple photodetectors. Each photodetector is configured to generate an electrical signal in response to light that falls on a light sensitive surface of the photodetector. The electrical signals generated by the photodetectors of the digitizer 150 include information from the sensors S1, S2, . . . SN about the sensed parameters. The information can be used by the monitoring/management processor 160 to determine the state of the battery 101 and/or to provide feedback to control battery operations.

In some implementations, the system includes at least N photodetectors. In some implementations, the system includes at least N pairs of photodetectors. These implementations are discussed in more detail below. An additional photodetector may be used to monitor intensity of the input light, e.g., by tapping off the input waveguide 141.

The management processor 160 may be configured to implement various processes that affect battery status based on the information provided by the sensors. According to various implementations, some aspects of the battery operation, e.g., charge rate and/or charge cycles, may be automatically controlled through a feedback output 161 from the management processor 160. The management processor 160 may use sensor information to make predictions and/or estimations regarding the state of the battery, e.g., state of health (SOH) and/or state of charge (SOC). These predictions and estimations may be developed using theoretical and/or empirical models and may be adaptable based on operational conditions of the battery, measures of internal and/or external parameters and/or correlations between the operational conditions and measured parameters. Some implementations may provide energy system monitoring only and thus may not include the management system components, and/or in some implementations the management system may not provide feedback to the energy system.

In some scenarios, information acquired or developed by the management processor 160 may be provided to an operator via an electronic or printed report. For example, the management processor 160 may compile, analyze, trend, and/or summarize the sensed parameters, and/or may perform other processes using the sensed parameters as input, such as predicting and/or estimating the state of the energy system 101. The results of these processes and/or other information derived from monitoring the energy system 101 may be provided in a report that can be displayed graphically or textually or in any convenient form to an operator and/or may be provided to another computer system for storage in a database and/or further analysis.

The sensors S1, S2, . . . SN disposed on the FO cable 130 may comprise any type (or multiple types) of optical sensor, including fiber Bragg grating (FBG) sensors and/or etalon or Fabry-Perot (FP) sensors. Both the FBG and etalon/FP sensors are collectively referred to herein as optical sensors. Although some examples provided below are based on FBG sensors, it will be understood that other types of optical sensors could alternatively or additionally be used in these and other embodiments.

Referring again to FIG. 1, light from the light source 110 travels through the FO cable 130 to the sensors S1, S2, . . . SN. The input light interacts with the FBG sensors S1, S2, . . . SN that are spaced apart along the FO cable 130. Each FBG sensor reflects a portion of the input light, and the reflected light is referred to as output light emanating from the optical sensor. The output light from all sensors travels through the FO 130 to the input waveguide 141 of the optical demultiplexer 140.

The FBG sensors can be formed by a periodic modulation of the refractive index along a finite length (typically a few mm) of the core of the FO cable. This pattern reflects a wavelength, called the Bragg wavelength, that is determined by the periodicity of the refractive index profile of the FBG sensor. In practice, the sensor typically reflects a narrow band of wavelengths centered at the Bragg wavelength. The Bragg wavelength at a characteristic or base value of the external stimulus is denoted $\lambda$, and light having a peak, center, or centroid wavelength $\lambda$ (and a narrow band of wavelengths near $\lambda$) is reflected from the sensor when it is in a predetermined base condition. For example, the base condition may correspond to 25 degrees C. and/or zero strain. When the sensor is subjected to an external stimulus, such as temperature, strain, or other such stimulus, the stimulus changes the periodicity of the grating and the index of refraction of the FBG, and thereby alters the reflected light so that the reflected light has a peak, center, or centroid wavelength, $\lambda_s$, different from the base wavelength, $\lambda$. The resulting wavelength shift, $\Delta\lambda/\lambda=(\lambda-\lambda_s)/\lambda$ is a proxy measure of the stimulus.

FBG sensors may be sensitive to changes in refractive index n, strain $\epsilon_1$, and ambient temperature changes $\Delta T$, for example. The refractive index n can be made sensitive to the chemical environment of the sensor by stripping the FO cladding over the sensor element region and/or by adding appropriate coatings to this sensitive area. Alternately, FBG sensors can be made sensitive to the chemical environment by applying special coatings that convert the chemical composition of the environment into a strain signal (e.g. hydrogen sensors based on palladium coatings). According to embodiments discussed herein, optical sensors such as FBG sensors are used to detect chemical composition changes in battery cells that might affect performance. An example of this is formation of a corrosive agent, hydrogen fluoride (HF), in Li-ion cells caused by moisture penetration.

The sensitivity of FBGs to temperature changes allows local temperatures within battery cells to be monitored. While this is useful in general for battery system management, it is particularly beneficial for early detection of thermal runaways. Thermal runaways affect many battery chemistries and can be devastating in Lithium-ion cells due to their high energy density. During a thermal runaway, the high heat of the failing cell can propagate to the next cell, causing it to become thermally unstable as well. In some cases, a chain reaction occurs in which each cell disintegrates at its own timetable. A pack of battery cells can be destroyed within a few seconds or can linger on for several hours as each cell is consumed one-by-one.

The sensitivity of the FBG sensors to strain allows embedding FBG sensors into battery electrodes to monitor the expansion/contraction cycles of the electrodes (which is useful for estimating charge levels, e.g. in Lithium-ion cells). Additionally, electrode strain measurements allow for examining the degradation of the electrodes, and thus the overall degradation of the battery. FBG sensitivity to strain also allows measurement of internal cell pressure by capturing cell wall strains.

In measuring energy system parameters using FBG sensors, it can be beneficial to distinguish between and quantify the individual contributions of the multiple parameters of interest. In some cases, a multi-sensor configuration may be used so that the parameter of interest can be compensated for the contributions of other parameters. For example, a two-sensor approach may be used for temperature-compensated chemical sensing, where the two sensors can be arranged in close proximity. In some implementations, a first sensor of the two sensors is exposed to temperature and is also exposed to the chemical environment by stripping its cladding. A second sensor of the two sensors used for compensation retains its cladding and is only sensitive to temperature. Similar configurations may be used for temperature-compensated strain measurements and strain-compensated temperature measurements.

For temperature-compensated strain measurements, two FBG sensors are placed in close proximity where the first sensor is exposed to strain and temperature and a second sensor used for compensation is exposed to temperature but not strain. The temperature measurement of the second sensor is used to compensate for temperature-induced changes in the reflected wavelength of the first sensor. For example, the first sensor may be placed within an electrode or cell wall of a battery and the second sensor may be placed nearby and/or at a location having about equal temperature as the location of the first sensor while being subjected to a known and/or non-varying strain. For example, the second sensor may be located near but not within the electrode or cell wall, or can be insulated from strain but not temperature via a thin-walled, electrically-insulating tube.

Fiber optic sensors, such as FBG sensors and etalon (Fabry-Perot) sensors may be used for monitoring systems. Fiber optic sensors have been demonstrated to withstand and perform in various harsh environments. The most common material used is silica, which is corrosion resistant, can withstand high tensile strain, and can survive between $-200°$ C. and $800°$ C. Silica-based FBG sensors provide repeatable temperature dependency of their peak wavelength, with no hysteresis, in tests done up to $300°$ C. It is expected that FBG sensors will survive long-term (13-25 years) in lead-acid batteries and at least up to a year in HF (a side product of Li-ion batteries; one year is expected to be longer than the life of the Li-ion battery after HF formation begins). Various types of plastic are also useful for FO cables and optical sensors. Fiber optic sensors such as FBG sensors are mechanically robust with respect to shock and vibration. Thus, embedded fiber optic sensors in energy storage/power systems such as batteries offer an attractive solution to reliably measure and monitor relevant parameters across various architectures and chemistries.

FBG-based sensing as illustrated in FIG. 1 allows for incorporating multiple sensing elements, e.g., about 64 sensors, on a single FO cable. In some approaches, each of the sensors S1, S2, . . . SN can be individually interrogated through wavelength domain multiplexing and demultiplexing. In some approaches, as illustrated below with reference to FIG. 11, sensors disposed in multiple sensor modules can be individually interrogated through a combination of time domain multiplexing and wavelength domain multiplexing and demultiplexing.

In some implementations, both ends of the sensor waveguide 130 disposed within a battery cell may be optically coupled to the light source 110 and the optical coupler 140 through optical switches (not shown in FIG. 1). Coupling both ends of the sensor waveguide may be useful in the event of a broken sensor waveguide. For example, consider the scenario wherein the FO cable 130 breaks in two portions between sensors S1 and S2, but both ends of the FO cable 130 are connected to the light source 110 and optical coupler 140 via optical switches. In this example, a single FO cable initially included all the sensors S1 through SN, but after the breakage, sensors S1 through SN can be considered to be disposed on two FO cables. Even with the broken FO cable, all sensors S1 through SN remain accessible through the two portions of the FO cable 130 if both ends of the FO cable are selectably optically coupled to the light source 110 and optical coupler 140 through an optical switch. The sensors on each portion of the broken FO cable are accessible by time multiplexing the signal from the FO cable portions. In the scenario outlined above, the signal from sensor S1 would be accessible through a first portion of broken FO cable 130 when the optical switches are in the first state and the signals from sensors S2 through SN would be accessible through the second portion of the broken FO cable 130 when the optical switches are in the second state.

In some embodiments the processor 160 may be capable of detecting that a sensor waveguide is broken, e.g., based on an absence of a signal at the wavelengths of the inaccessible sensors. If the processor detects a broken cable, it may be configured to initiate monitoring of all sensors of the FO cable through both portions of the broken FO cable. Coupling both ends of the FO cable may be useful in the implementation wherein only one sensor is disposed on the FO cable. For example, consider the scenario wherein the FO cable only includes S1. If the FO cable breaks between the light source and optical coupler and S1, then S1 would be inaccessible unless both ends of the FO cable are optically coupled to the light source and optical coupler as discussed above.

Figure 2:
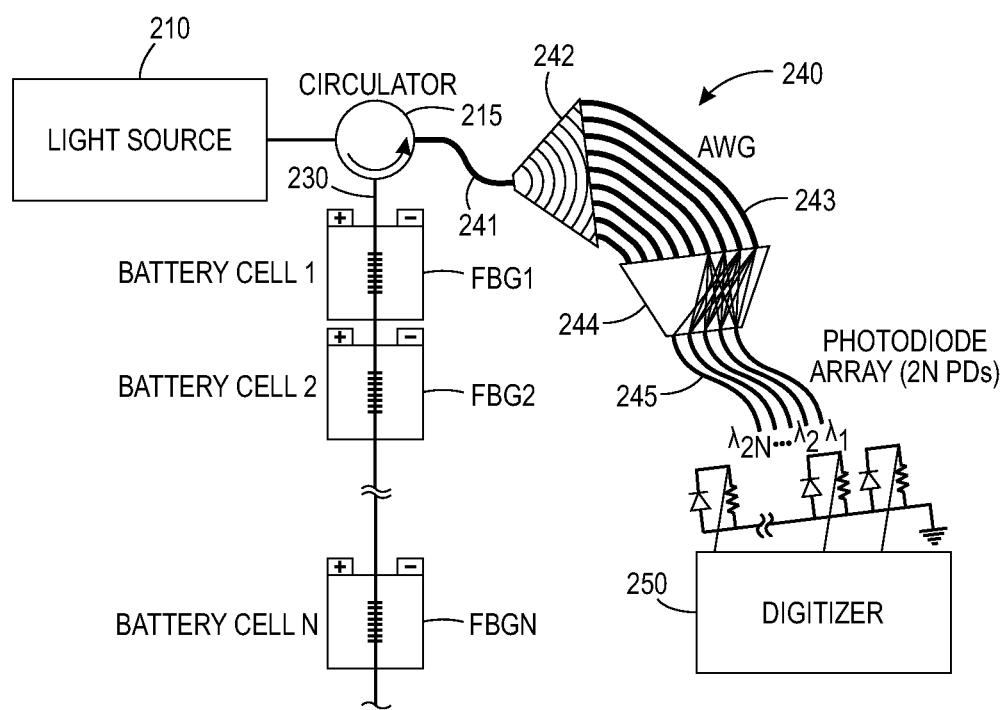
FIG. 2 illustrates wavelength domain multiplexing for multiple sensors using an arrayed waveguide grating (AWG) designed for sensing applications.

Embodiments disclosed herein involve wavelength domain multiplexing and demultiplexing for multiple sensors using an arrayed waveguide grating (AWG) designed for sensing applications as illustrated in FIG. 2. FIG. 2 illustrates a number of battery cells, Battery Cell 1, Battery Cell 2, . . . Battery Cell N, each battery cell respectively having an FBG sensor, FBG1, FBG2, . . . FBGN, disposed within, on, or about the battery cell. FBG1 operates in a wavelength band having peak, center, or centroid wavelength $\lambda_1$, FBG2 operates in a wavelength band having peak, center, or centroid wavelength $\lambda_2$, and FBGN operates in a wavelength band having center wavelength $\lambda_N$. Each FBG may be most sensitive to a different parameter, such that FBG1 is most sensitive to parameter 1, FBG2 is most sensitive to parameter 2, and FBGN is most sensitive to parameter N. A change in parameter 1 may shift the wavelength of the light reflected from FBG1 from $\lambda_1$ to $(\lambda_1+/-\Delta_1)$, a change in parameter 2 may shift the wavelength of light reflected from FBG2 from $\lambda_2$ to $(\lambda_2+/-\Delta_2)$, etc. The wavelength shifts caused by changes in the sensed parameters are small compared to the spacing between the characteristic base wavelengths of the individual FBGs. Therefore, it is feasible to separate the information from the different FBGs using dispersive elements such as arrayed waveguide gratings, linear variable filters and/or other dispersive elements in an optical wavelength domain demultiplexing scheme. As discussed in more detail below, an optical time domain multiplexing scheme can optionally be implemented and can be used in conjunction with the wavelength domain demultiplexing.

Light source 210 is configured to provide input light to the FBGs through circulator 215. The light source 210 has a bandwidth broad enough to provide input light for each of the FBG sensors and over the range of reflected wavelengths expected. The AWG may include N pairs of output waveguides 245, wherein each pair of output waveguides 245 is centered in wavelength around the reflection output of a particular FBG. Light from the light source travels through the circulator and reflects off the FBGs as output light. The output light emanating from the FBGs is carried on sensor optical waveguide 230 through circulator 215 to the AWG 240 which is used as an optical wavelength domain demultiplexer. When used as an optical demultiplexer, light from the AWG input waveguide 241 is dispersed via diffraction to output waveguides 245 depending on the wavelength of the light. For example, an AWG might have a center wavelength of 1550 nm, and 16 output channels with a channel spacing of 100 GHz (0.8 nm at that wavelength). In this scenario, light input at 1549.6 nm will go to channel 8, and light input at 1550.4 nm will go to channel 9, etc.

An AWG may include an input waveguide 241, a first slab waveguide 242, array waveguides 243, a second slab waveguide 244, and output waveguides 245. Each of the array waveguides 243 is incrementally longer than the next. The input light is broken up in the first slab waveguide 242 among the array waveguides 243. At the output of each array waveguide 243, the light has accrued a wavelength-dependent phase shift, which also is incrementally more from one waveguide to the next. The outputs of the array waveguides 243 resemble an array of coherent sources. Therefore, the propagation direction of the light emitted from the array waveguides 243 into the second slab waveguide 244 depends on the incremental phase shift between the sources and hence the wavelength, as in a diffraction grating.

In some embodiments, the optical coupler, e.g., AWG, the photodiode array and/or the digitizer may be arranged as a planar lightwave circuit, i.e., integrated optical device. For example, these system components may be made from silicon-on-insulator (SOI) wafers using optical and/or electron beam lithography techniques. The planar lightwave circuit can be coupled to the fiber optic, aligned using V-grooves anisotropically etched into the silicon. Hybrid integration with other semiconductors, for example germanium, is possible to provide photodetection at energies below the bandgap of silicon.

In the AWG 240, the outputs of the array waveguides 243 (and hence the input side of the slab waveguide 244) may be arranged along an arc with a given radius of curvature such that the light emanating from them travels in the second slab waveguide 244 and comes to a focus a finite distance away. The inputs of the output waveguides 245 are nominally disposed at the focal points corresponding to specific wavelengths, although they may be set either in front of or behind the foci to deliberately introduce "crosstalk" between the output waveguides as will be described later. Therefore, light at the input 241 of the AWG 240 is passively routed to a given one of the output waveguides 245 depending on wavelength of the light. Thus, the output light from the sensors FBG1, FBG2, FBGN is routed to output waveguides 245 depending on the wavelength of the output light.

The output waveguides 245 are optically coupled to a digitizer 250 that includes photodetectors, e.g., 2N photodetectors. Due to the wavelength-based spatial dispersion in the AWG, the output light from the sensors FBG1, FBG2, . . . FBGN is spatially distributed across the surface of the digitizer. The photodetectors sense the light from the output waveguides and generate electrical signals that include information about the sensed parameters.

Figure 3:
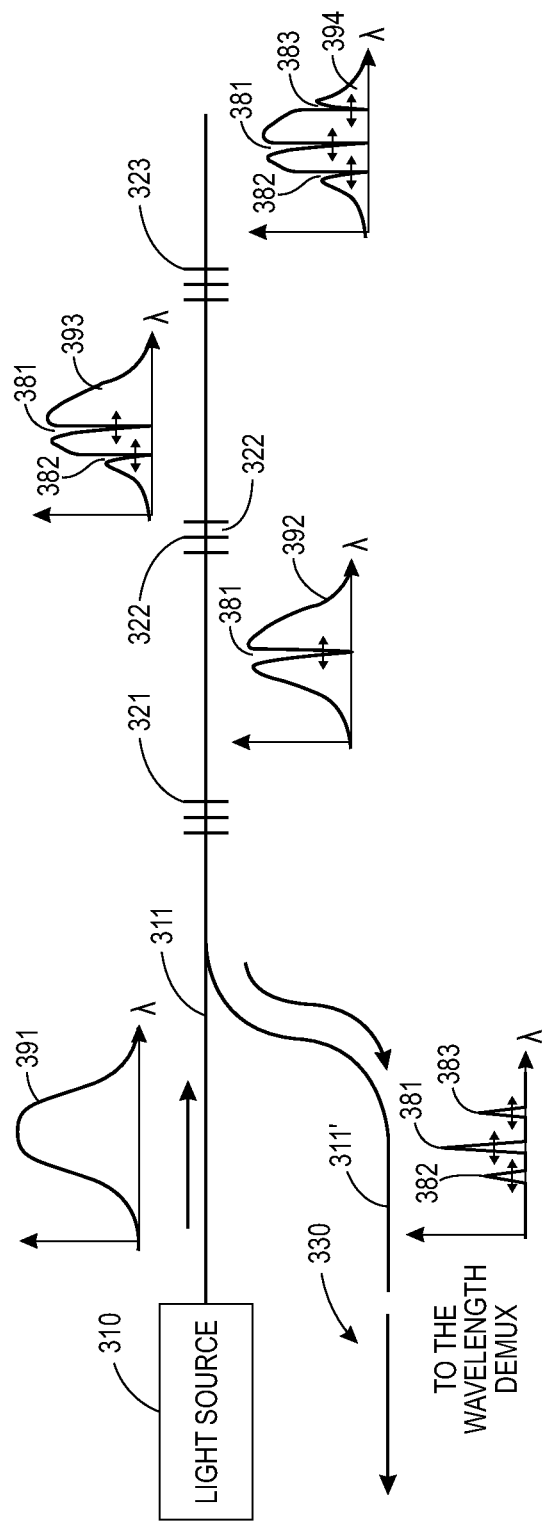
FIG. 3 illustrates reflected spectra for fiber Bragg grating (FBG) sensors.

FIG. 3 illustrates operation of an energy storage/power system with optically multiplexed sensor outputs. As indicated in FIG. 3, broadband light is transmitted by the light source 310, which may comprise or be a light emitting diode (LED) or superluminescent laser diode (SLD), for example. The spectral characteristic (intensity vs. wavelength) of the broadband light is shown by inset graph 391. The light is transmitted via the FO cable 311 to the first FBG sensor 321. The first FBG sensor 321 reflects a portion of the light in a first wavelength band having a peak, center, or centroid wavelength, $\lambda_1$. Light having wavelengths other than within the first wavelength band is transmitted through the first FBG sensor 321 to the second FBG sensor 322. The spectral characteristic of the light transmitted to the second FBG sensor 322 is shown in inset graph 392 and exhibits a notch at the first wavelength band centered at $\lambda_1$ indicating that light in this wavelength band is reflected by the first sensor 321.

The second FBG sensor 322 reflects a portion of the light in a second wavelength band having a central or peak wavelength, $\lambda_2$. Light that is not reflected by the second FBG sensor 322 is transmitted through the second FBG sensor 322 to the third FBG sensor 323. The spectral characteristic of the light transmitted to the third FBG sensor 323 is shown in inset graph 393 and includes notches centered at $\lambda_1$ and $\lambda_2$.

The third FBG sensor 323 reflects a portion of the light in a third wavelength band having a central or peak wavelength, $\lambda_3$. Light that is not reflected by the third FBG sensor 323 is transmitted through the third FBG sensor 323. The spectral characteristic of the light transmitted through the third FBG sensor 323 is shown in inset graph 394 and includes notches centered at $\lambda_1$, $\lambda_2$, and $\lambda_3$.

Light in wavelength bands 381, 382, 383, having central wavelengths $\lambda_1$, $\lambda_2$ and $\lambda_3$ (illustrated in inset graph 395) is reflected by the first, second, or third FBG sensors 321, 322, 323, respectively, along the FO cables 311 and 311' to an the optical wavelength demultiplexer. From the wavelength demultiplexer, the sensor light may be routed to a digitizer/analyzer. The digitizer/analyzer may compare the shifts in each of the central wavelengths $\lambda_1$, $\lambda_2$ and $\lambda_3$ and/or wavelength bands reflected by the sensors 321-323 to a characteristic base wavelength (a known wavelength) to determine whether changes in the parameters sensed by the sensors 321-323 have occurred. The digitizer/analyzer may determine that the one or more of the sensed parameters have changed based on the wavelength analysis and may calculate a relative or absolute measurement of the change.

In some cases, instead of emitting broadband light, the light source may scan through a wavelength range, emitting light in narrow wavelength bands to which the various sensors disposed on the FO cable are sensitive. The reflected light is sensed during a number of sensing periods that are timed relative to the emission of the narrowband light. For example, consider the scenario where sensors 1, 2, and 3 are disposed on a FO cable. Sensor 1 is sensitive to a wavelength band (WB1), sensor 2 is sensitive to wavelength band WB2, and sensor 3 is sensitive to WB3. The light source may be controlled to emit light having WB1 during time period 1 and sense reflected light during time period 1a that overlaps time period 1. Following time period 1a, the light source may emit light having WB2 during time period 2 and sense reflected light during time period 2a that overlaps time period 2. Following time period 2a, the light source may emit light having WB3 during time period 3 and sense reflected light during time period 3a that overlaps time period 3. Using this version of time domain multiplexing, each of the sensors may be interrogated during discrete time periods.

The FO cable used for energy storage/power system monitoring may comprise a single mode (SM) FO cable (as depicted in FIG. 3) or may comprise a multi-mode (MM) FO cable. While single mode fiber optic cables offer signals that are easier to interpret, to achieve broader applicability and lower costs of fabrication, multi-mode fibers may be used.

MM fibers may be made of plastic rather than silica, which is typically used for SM fibers. Plastic fibers may have smaller turn radii when compared with the turn radii of silica fibers. This can offer the possibility of curved or flexible configurations when plastic fibers are embedded into battery cells and in individual cells of fuel cell stacks, for example. Furthermore, MM fibers can work with less expensive light sources (e.g., LEDs) as opposed to SM fibers that may need more precise alignment with superluminescent diodes (SLDs). Therefore, sensing systems based on optical sensors in MM fibers may yield lower cost systems.

Figure 4:
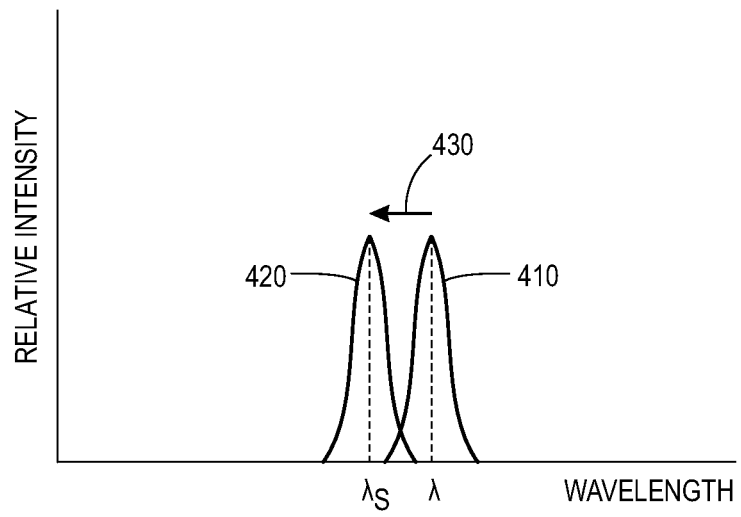
FIG. 4 shows an idealized shift in the wavelength spectrum for a FBG sensor deployed on a single mode fiber cable.

FIG. 4 is an idealized representation of light reflected from a FBG sensor deployed on a SM FO cable. In the characteristic base or known state, the FBG sensor reflects light in a relatively narrow wavelength band 410 having a centroid wavelength, $\lambda$. After the FBG sensor experiences a change in the sensed condition, e.g., a change in temperature, strain, chemical environment, the light reflected by the sensor shifts to a different wavelength band 420 having a centroid wavelength $\lambda_s$. Wavelength band 420 is similar in width, amplitude and other morphological characteristics when compared to wavelength band 410, but the centroid wavelength, $\lambda_s$, of wavelength band 420 is shifted 430 from the centroid wavelength, $\lambda$, of wavelength band 410 by an amount that is related to the change in the sensed condition. Wavelength bands of similar widths can be identified as wavelength bands having similar full width half maximum (FWHM) values, for example.

Figure 5:
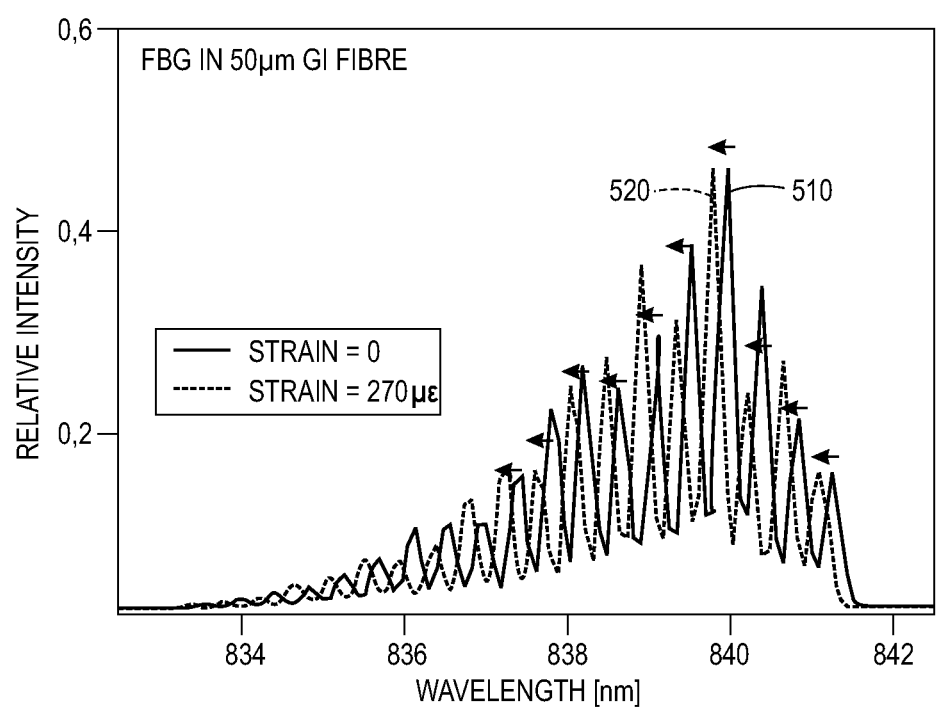
FIG. 5 shows the shift in the wavelength spectrum for a FBG sensor deployed on a multi-mode fiber optic cable.

FIG. 5 depicts actual data from an FBG sensor deployed on a MM FO cable. FBG sensors deployed on MM FO cables reflect light in multiple wavelength bands in contrast to FBG sensors on SM FO cable where only one wavelength band is reflected by the grating. In the characteristic base condition, the sensor reflects a characteristic spectrum that may include multiple narrower wavelength bands (also referred to as modes) as shown in graph 510. When a change in the sensed parameter occurs, the reflected wavelength spectrum 520 substantially maintains its shape, but is shifted in wavelength in response to the sensed condition. Approaches discussed herein may be extendable to interrogate MM FBG sensors.

Figure 6A:
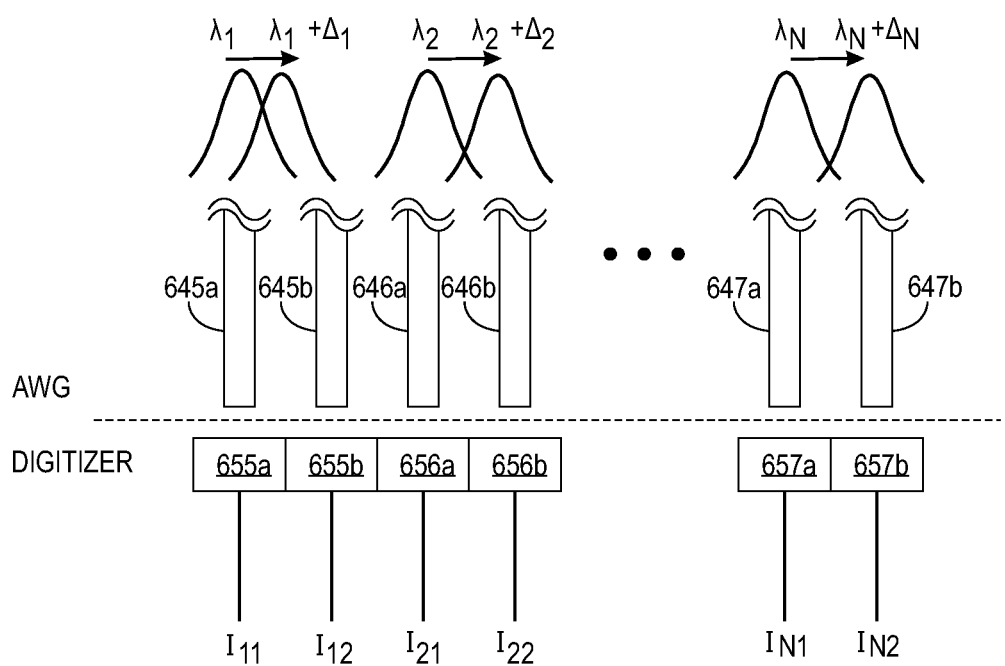
FIGS. 6A, 6B and 7 illustrate in more detail the output waveguides of an AWG used as a wavelength domain optical demultiplexer and a digitizer according to some embodiments.

FIG. 6A illustrates in more detail the output waveguides of an AWG used as a wavelength domain optical demultiplexer (e.g. element 140 of FIG. 1) and a digitizer (e.g., element 150 of FIG. 1) according to some embodiments. In this configuration 2N photodetectors are respectively coupled to receive light from N sensors. The AWG spatially disperses sensor output light having centroid wavelengths $\lambda_1, \lambda_2, \ldots \lambda_N$ to the output waveguide pairs 645a,b, 646a, b, ... 647a,b. Sensor output light having centroid wavelength $\lambda_1$ is dispersed to waveguide pairs 645a, 645b; sensor output light having centroid wavelength $\lambda_2$ is dispersed to waveguide pairs 646a, 646b; sensor output light having centroid wavelength $\lambda_N$ is dispersed to waveguide pairs 647a, 647b, etc. Light from output waveguide 645a is optically coupled to photodetector 655a which generates signal $I_{11}$ in response to the detected light; light from output waveguide 645b is optically coupled to photodetector 655b which generates signal $I_{12}$ in response to the detected light; light from output waveguide 646a is optically coupled to photodetector 656a which generates signal $I_{21}$ in response to the detected light; light from output waveguide 646b is optically coupled to photodetector 656b which generates signal $I_{22}$ in response to the detected light; light from output waveguide 647a is optically coupled to photodetector 657a which generates signal $I_{N1}$ in response to the detected light; light from output waveguide 647b is optically coupled to photodetector 657b which generates signal $I_{N2}$ in response to the detected light.

As the centroid of a sensor's output light shifts in response to the sensed parameter, the AWG causes the spatial position of the sensor's output light to also shift. For example if sensor output light that initially has a centroid at $\lambda_1$ shifts to a centroid at $\lambda_1+\Delta_1$, as shown in FIG. 6A, the amount of light carried by output waveguide 645a decreases and the amount of light carried by output waveguide 645b increases. Thus, the amount of light detected by photodetector 655a decreases and the amount of light detected by photodetector 655b increases with corresponding changes in the photocurrents $I_1$ and $I_2$. Thus, a shift in the sensed parameter causes a shift in the sensor output light centroid from $\lambda_1$ to $\lambda_1+\Delta_1$ which in turn causes a change in the ratio of $I_{11}$ to $I_{12}$.

The photocurrent of each photodiode may be converted into a voltage with a resistor or transimpedance amplifier, and sensed and digitized. The wavelength shift may be calculated for the $i^{th}$ FBG with the following formula:

$$\lambda_i \approx \lambda_{i0} + \frac{\Delta\lambda}{2} \frac{I_{2i} - I_{2i-1}}{I_{2i} + I_{2i-1}}$$

Here, $\lambda_i$ is the estimated wavelength of the $i^{th}$ FBG, $\lambda_{i0}$ is the center wavelength of an output waveguide pair, $\Delta\lambda$ is the wavelength spacing between the peak transmission wavelengths of an output waveguide pair, and $I_{2i}$ and $I_{2i-1}$ are the light intensities recorded by the photodetectors at the output of each waveguide in the pair. From the sensed wavelength shift of a given FBG, it is possible to calculate values of sensed parameters, and in turn, to calculate properties of the battery or other energy systems corresponding to the parameters sensed by the FBG if it is known how those properties tend to vary the observed wavelength shift. In some embodiments, the FBGs have a FWHM roughly equal to $\Delta\lambda/2$, such that as the reflected peak from the FBG shifts from one photodetector in the pair to the other, there is a continuous and monotonic change in the differential signal of the pair (numerator in the formula above).

Figure 6B:
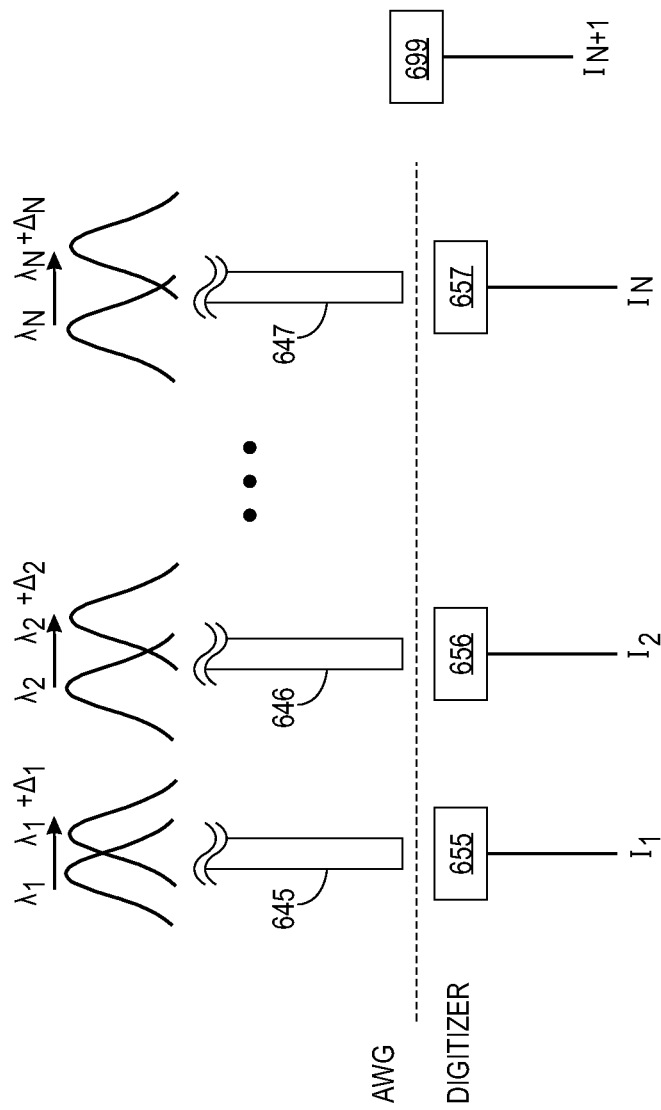

FIG. 6B illustrates in more detail another configuration of the output waveguides of an AWG used as a wavelength domain optical demultiplexer (e.g. element 140 of FIG. 1) and a digitizer (e.g., element 150 of FIG. 1) according to some embodiments. In this configuration N photodetectors are respectively coupled to receive light from N sensors. The AWG spatially disperses sensor output light having centroid wavelengths $\lambda_1, \lambda_2, \ldots \lambda_N$ to the output waveguides 645, 646, . . . 647. Sensor output light having centroid wavelength $\lambda_1$ is dispersed to waveguide 645; sensor output light having centroid wavelength $\lambda_2$ is dispersed to waveguide 646; sensor output light having centroid wavelength $\lambda_N$ is dispersed to waveguide 647, etc. Light from output waveguide 645 is optically coupled to photodetector 655 which generates signal $I_1$ in response to the detected light; light from output waveguide 646 is optically coupled to photodetector 656 which generates signal $I_2$ in response to the detected light; light from output waveguide 647 is optically coupled to photodetector 657 which generates signal $I_N$ in response to the detected light.

As the centroid of a sensor's output light shifts in response to the sensed parameter, the AWG causes the spatial position of the sensor's output light to also shift. For example, if sensor output light that initially has a centroid at $\lambda_1$ shifts to a centroid at $\lambda_1+\Delta_1$ as shown in FIG. 6B, the amount of light carried by output waveguide 645 increases. Thus, the amount of light detected by photodetector 655 increases with a corresponding change in the photocurrent $I_1$. Thus, a shift in the sensed parameter causes a shift in the sensor output light centroid from $\lambda_1$ to $\lambda_1+\Delta_1$, which in turn causes a change in the current $I_1$.

Changes in the photodetector current that are caused by fluctuations of light source intensity (e.g., 110 in FIG. 1) can be differentiated from changes in photodetector current caused by wavelength shifts in sensor output light by measuring the light source intensity with an additional photodetector 699 that generates current $I_{N+1}$. Then, a wavelength shift can be calculated from the ratio $I_1/I_{N+1}$ for sensor 1, $I_2/I_{N+1}$ for sensor 2, etc.

From the sensed wavelength shift of a given FBG, it is possible to calculate a value of sensed parameter, and in turn, to calculate properties of the battery or other energy systems corresponding to the parameter sensed by the FBG if it is known how those properties tend to vary the observed wavelength shift.

Figure 7:
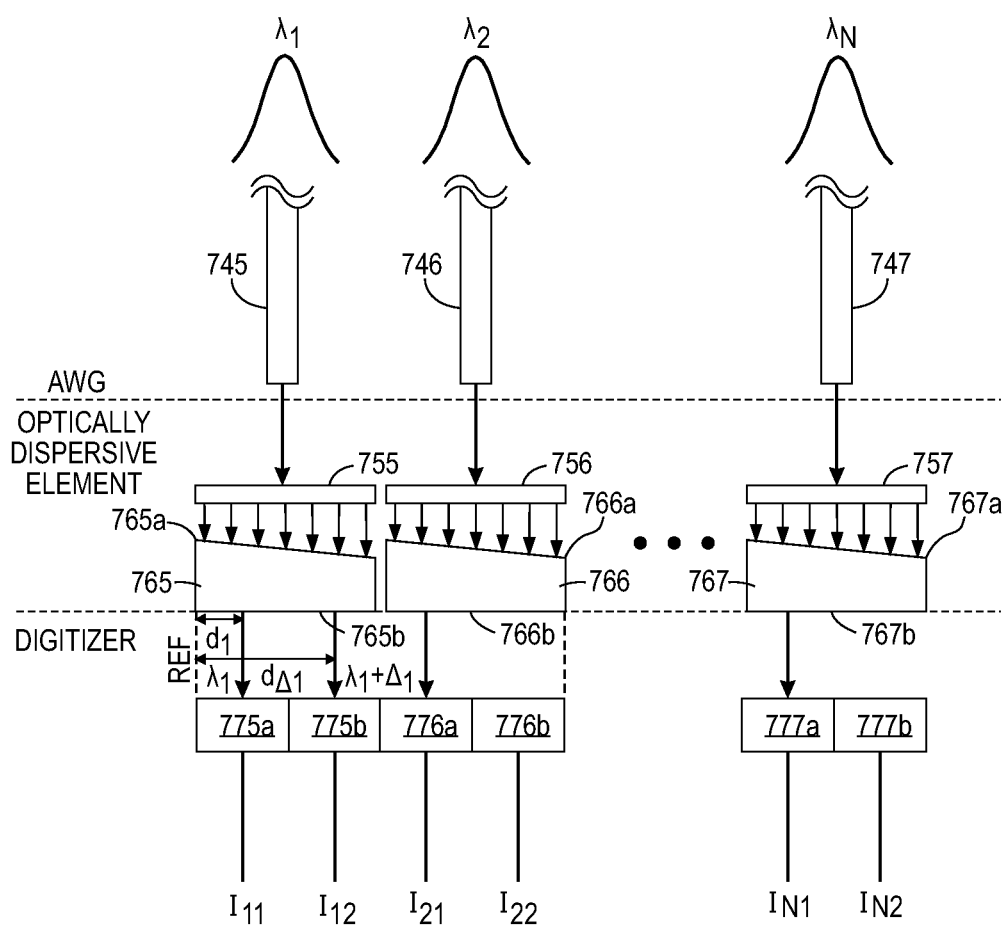

FIG. 7 illustrates in more detail the output waveguides of an AWG used as a wavelength domain optical demultiplexer, an additional dispersive element, and a digitizer according to some embodiments. In this example, the output light from sensors 1, 2 . . . N having initial centroid wavelengths $\lambda_1$, $\lambda_2, \ldots \lambda_N$ is respectively spatially dispersed to output waveguides 745, 746, . . . 747 of the AWG. The light from output waveguides 745, 746, . . . 747 is incident on a linearly variable transmission structure (LVTS) 765, 766, . . . 767 or other spatially dispersive optical element.

Optionally, the LVTS includes spreading components 755, 756 . . . 757 configured to collimate and/or spread the light from the output waveguide 745, 746 . . . 747 across an input surface of LVTS 765, 766, . . . 767. In arrangements where sufficient spreading of the light occurs from the output waveguides 745, 746, . . . 747, the spreading components may not be used. The LVTS 765, 766, . . . 767 comprises a dispersive element, such as a prism or a linear variable filter. The LVTS 765, 766, . . . 767 receives light at its input surface 765a, 766a, . . . 767a from the waveguide 745, 746, . . . 747 and (optionally) the spreading component 755, 756, . . . 757 and transmits light from its output surface 765b, 766b, . . . 767b to photodetector pairs 775, 776, . . . 777. At the output surface 765b, 766b, . . . 767b of the LVTS 765, 766, . . . 767, the wavelength of the light varies with distance along the output surface. Thus, the LVTS 765, 766, . . . 767 can serve to further demultiplex the optical signal incident at the input surface 765a, 766a, . . . 767a of the LVTS 765, 766, . . . 767 according to the wavelength of the light.

FIG. 7 shows two wavelength bands emitted from the LVTS 765, an initial emission band has a centroid wavelength of $\lambda_1$ emitted at distance $d_1$ from a reference position (REF) along the output surface 765b. In response to the sensed parameter, the initial wavelength band shifts to a wavelength band having centroid wavelength $\lambda_1+\Delta_1$. The shifted wavelength band is emitted at distance $d_{\Delta 1}$ from the reference position.

A photodetector pair 775 is positioned relative to the LVTS 765 so that light transmitted through the LVTS 765 falls on the photodetector pair 775. For example, light having wavelength $\lambda_1$ may fall predominantly on photodetector 775a and light having wavelength $\lambda_1+\Delta_1$ may fall predominantly on photodetector 775b. The photodetector 775a generates signal $I_{11}$ in response to light falling on its light sensitive surface and photodetector 775b generates signal $I_{12}$ in response to light falling on its light sensitive surface. The signals $I_{11}$, $I_{12}$ include information about the sensed parameter such that a change in the ratio of $I_{11}$ and $I_{12}$ indicates a change in the sensed parameter, which can be calculated using the equation discussed above.

Figure 8:
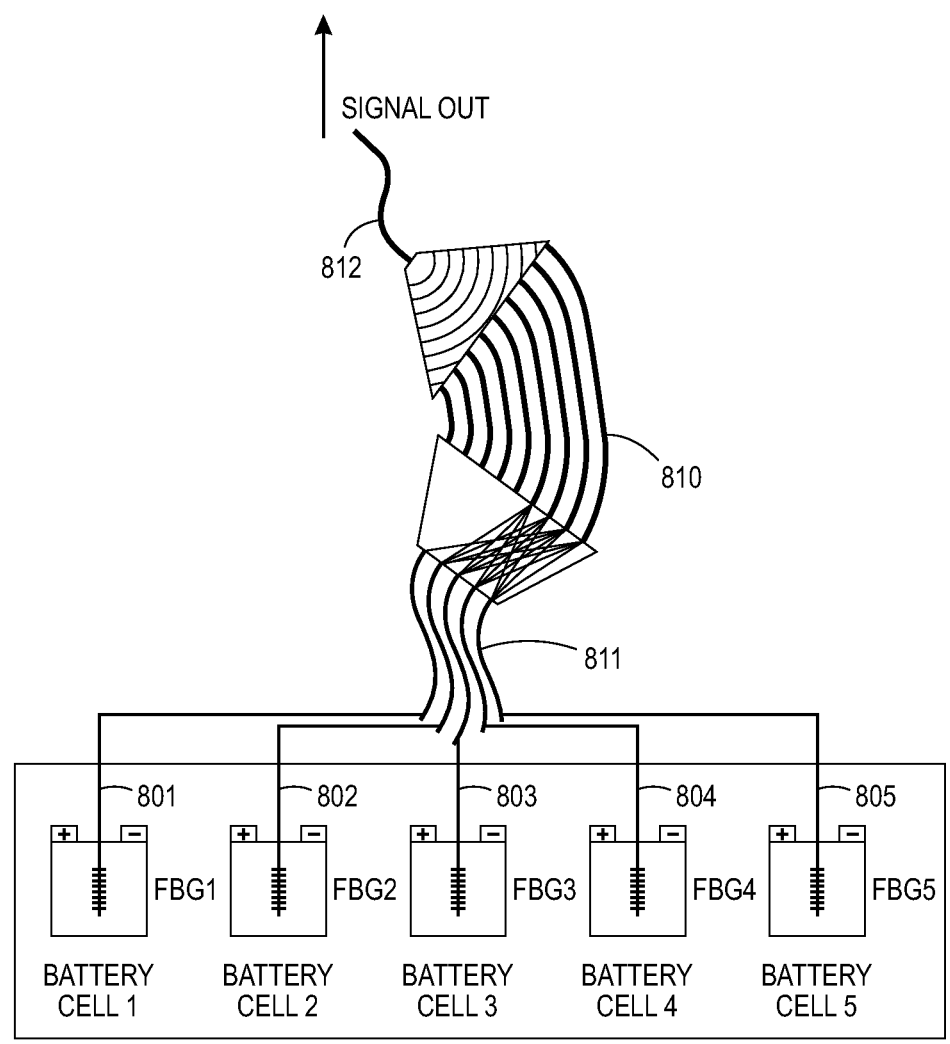
FIG. 8 shows a portion of a monitoring system including multiple FBG sensors in accordance with some embodiments.

FIG. 8 shows a portion of a monitoring system including multiple FBG sensors, FBG1, FBG2, FBG3, FBG4, FBG5 respectively disposed on multiple sensor waveguides, 801, 802, 803, 804, 805 inserted in battery cells Battery Cell 1, Battery Cell 2, Battery Cell 3, Battery Cell 4, Battery Cell 5. Each of the multiple sensor waveguides is respectively optically connected to an input waveguide 811 of AWG 810. The output light from each of the FBG sensors is multiplexed by AWG 810 onto waveguide 812 that may be optically coupled to a circulator and light source (as in 230 of FIG. 2) which is then connected to an input waveguide of a wavelength domain demultiplexer, such as AWG 240 shown in FIG. 2.

Traditionally, AWGs have been used in high speed communication systems and are designed to minimize crosstalk between adjacent channels. This is important for digital communications because the bit error rate must be made very low (on the order of $10^{-12}$) so it is suboptimal for light from one channel to leak into the next. Embodiments described herein involve AWGs specifically designed for sensing applications. These AWGs deliberately introduce crosstalk between adjacent channels.

Figure 9A:
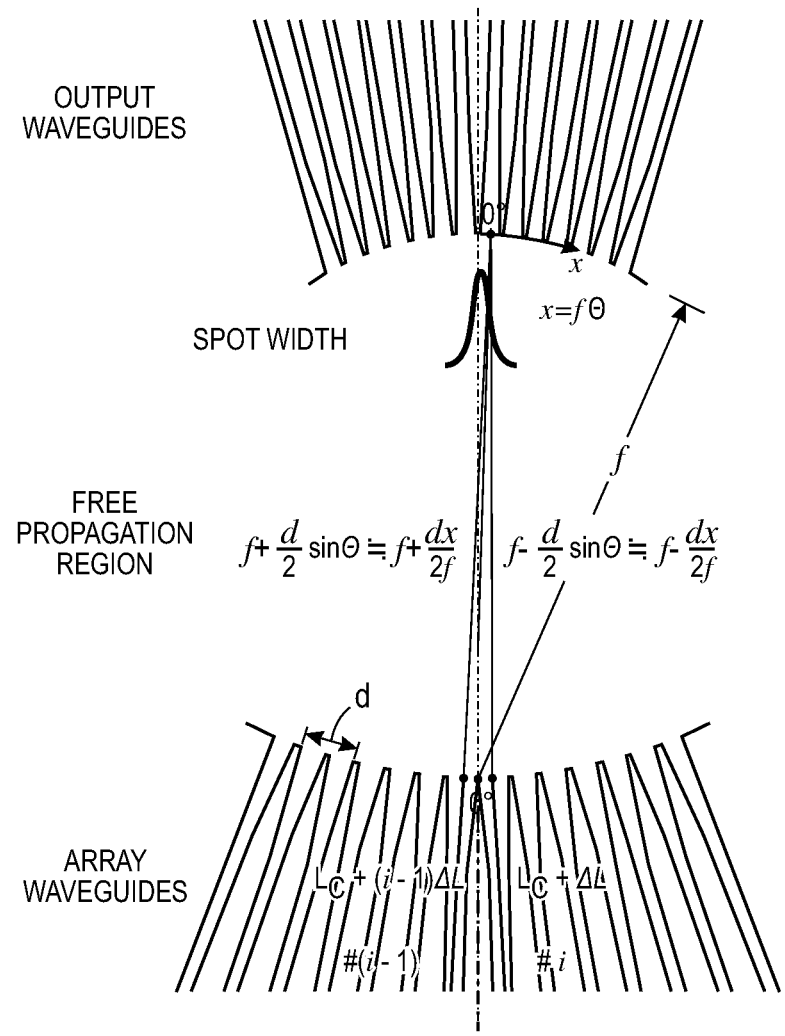
FIGS. 9A and 9B show portions of AWGs and illustrate techniques for deliberately introducing crosstalk into the output waveguide signals in accordance with some embodiments.

In some embodiments, AWGs with crosstalk are configured so that the center-to-center spacing between adjacent output waveguides in a pair of output waveguides is less than the optical spot size at the output waveguides, where the optical spot size is the full width half maximum (FWHM) of the intensity of the spot. In FIG. 9A, the output coupler of an AWG is shown with the spacing of the output waveguides decreased from "normal" telecom operation to introduce crosstalk between adjacent channels. Here, there is an incremental length between adjacent array waveguides of ΔL. This increment is nominally chosen as a multiple m of the center wavelength of the AWG (where m represents the diffraction order of the AWG), so that light exits from the center output waveguide at the center wavelength of the AWG. The spacing of the array waveguides is d, and the change in position of the optical spot at the input of the output waveguides for a change in wavelength Δλ is given as:

$$\Delta x \approx mf\Delta\lambda/d,$$

where f is the distance from the array waveguides to the output waveguides (note the radius of curvature of both the input and output side of the slab waveguide is also f, so that the optical spot comes to a focus at the output waveguides).

The spacing of a pair of output waveguides should represent a translation of the spot from mostly on one waveguide to mostly on the other waveguide as the FBG's reflected wavelength translates over its range. That is, for a change in reflected center wavelength Δλ, the spacing of the pair should be chosen according to the formula above. However, the center wavelength of different pairs of output waveguides should be tailored so as to not cause interference between the different pairs (for example, if 8 channels are equally spaced in an AWG, using channels 1 and 2 for the first sensor, 4 and 5 for the second sensor, and 7 and 8 for the third sensor would provide adequate isolation between the sensor readouts in some circumstances).

In some embodiments, the optical spot size at a pair of output waveguides is on the order of the lateral translation of the spot expected over the range of operation of the sensor, which should in turn be on the order of the pair spacing. If the spot is too broad compared to the spacing, the differential signal between the two output waveguides within the pair will be small, and if it is too narrow, the dynamic range of the sensor will be limited. The spot size can be estimated from diffraction considerations to be roughly 2fλ/Kd, where K is the number of array waveguides and λ is the operating wavelength.

There are at a number of methods that may be used to adjust the spot size relative to the channel spacing, e.g., by decreasing the output waveguide spacing, by increasing the spot size at the input of the output waveguides; and/or by moving the output waveguides away from the focal point of the array waveguides.

Figure 9B:
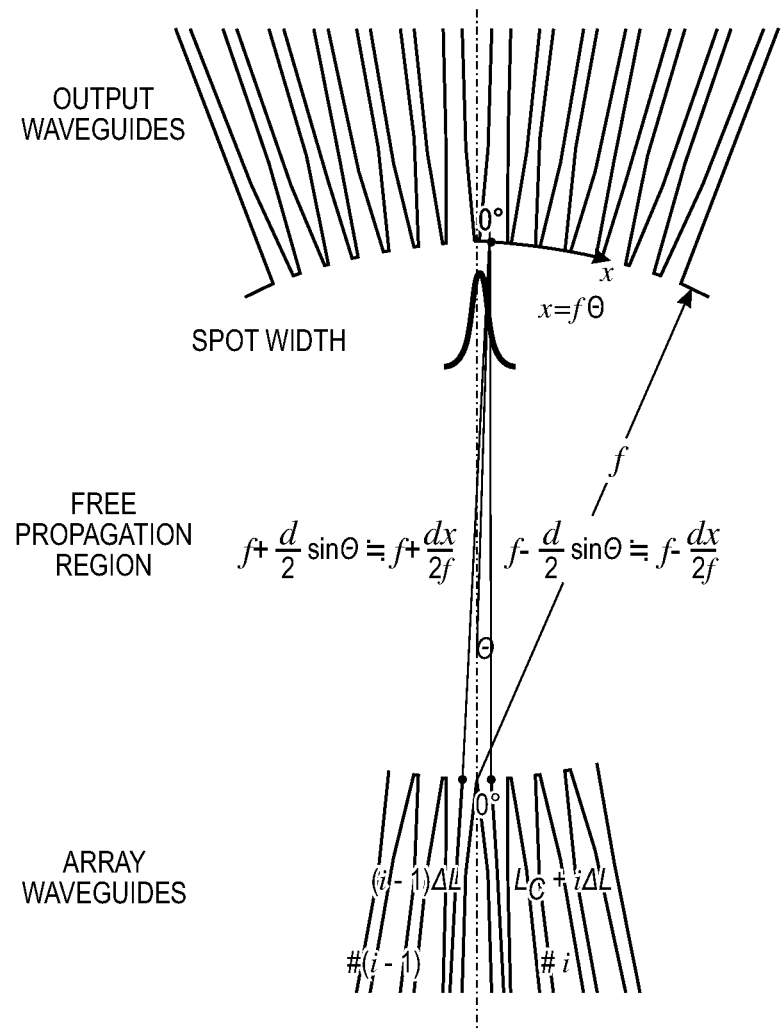

In FIG. 9A, the channel spacing/spot size ratio is adjusted by keeping the spot size fixed (assuming it is already the proper size for operation, e.g., to provide optimal operation), but decreasing the output waveguide spacing. In FIG. 9B, the channel spacing is assumed to be sufficient, e.g., optimal, according to the above considerations, but the spot size is increased to be within its optimal range by decreasing the number of array waveguides K. We can find a good value of K by combining the equations above if we set $$\Delta x \approx \frac{mf\Delta\lambda}{d} = \frac{2f\lambda}{Kd},$$

so K≈2λ/mΔλ. In addition, adjusting the spot size relative to the channel spacing may be implemented by moving the output waveguides away from the focal length $f_0$ of the array waveguides to a new distance f, such that the spot size becomes roughly $Kd|f-f_0|/f_0$.

Figure 10:
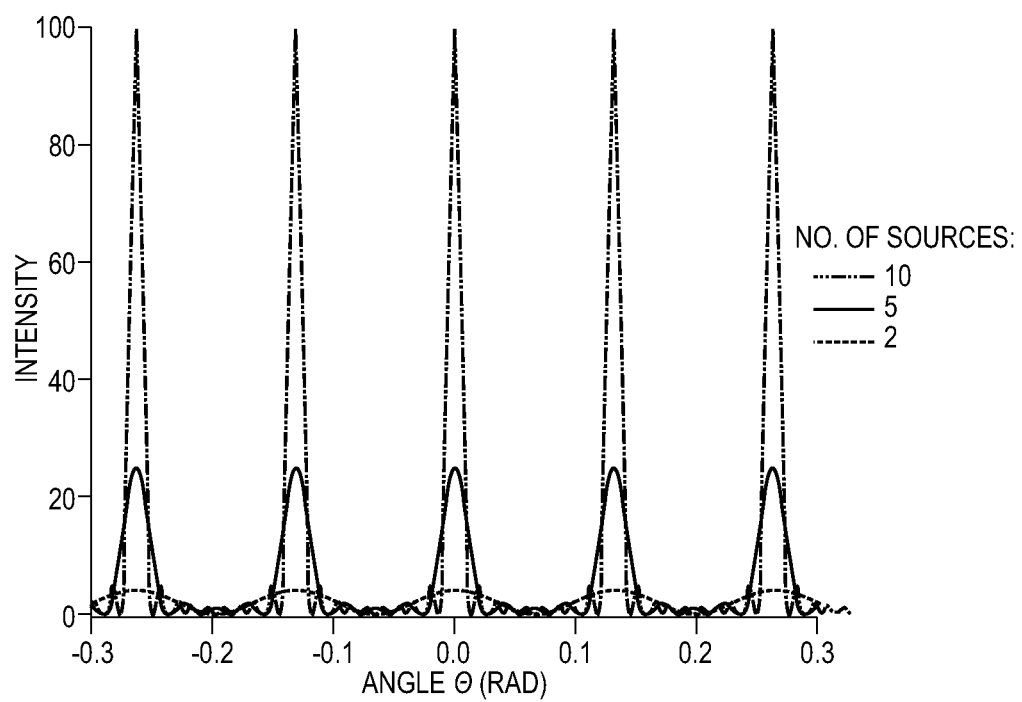
FIG. 10 is a graph showing that a decreasing the number of sources broadens the angular distribution of the light emanating from an array of coherent sources.

As shown in FIG. 10, decreasing the number of sources broadens the angular distribution of the light emanating from an array of coherent sources. This phenomenon can be understood in analogy to a smaller lens having poorer diffraction-limited performance compared to a bigger lens. Therefore, even a relatively narrow spectral peak can be distributed across two channels so that an intensity-independent wavelength shift can be detected.

It is often the case that many more FBGs need to be sensed than there are available photodiodes/output channels of the AWG. Therefore, in some embodiments, optical time domain multiplexing is used in conjunction with the previously described optical wavelength division multiplexing and demultiplexing. For each input of a multi-input AWG, there is a known wavelength-dependent mapping to the output waveguides. Therefore, time division multiplexing and wavelength division demultiplexing can be combined to address a far greater number of sensors than could be addressed with either method alone. In addition, the optical switches could be integrated onto the same substrate as the AWG allowing fabrication of modules having an identical structure.

Figure 11:
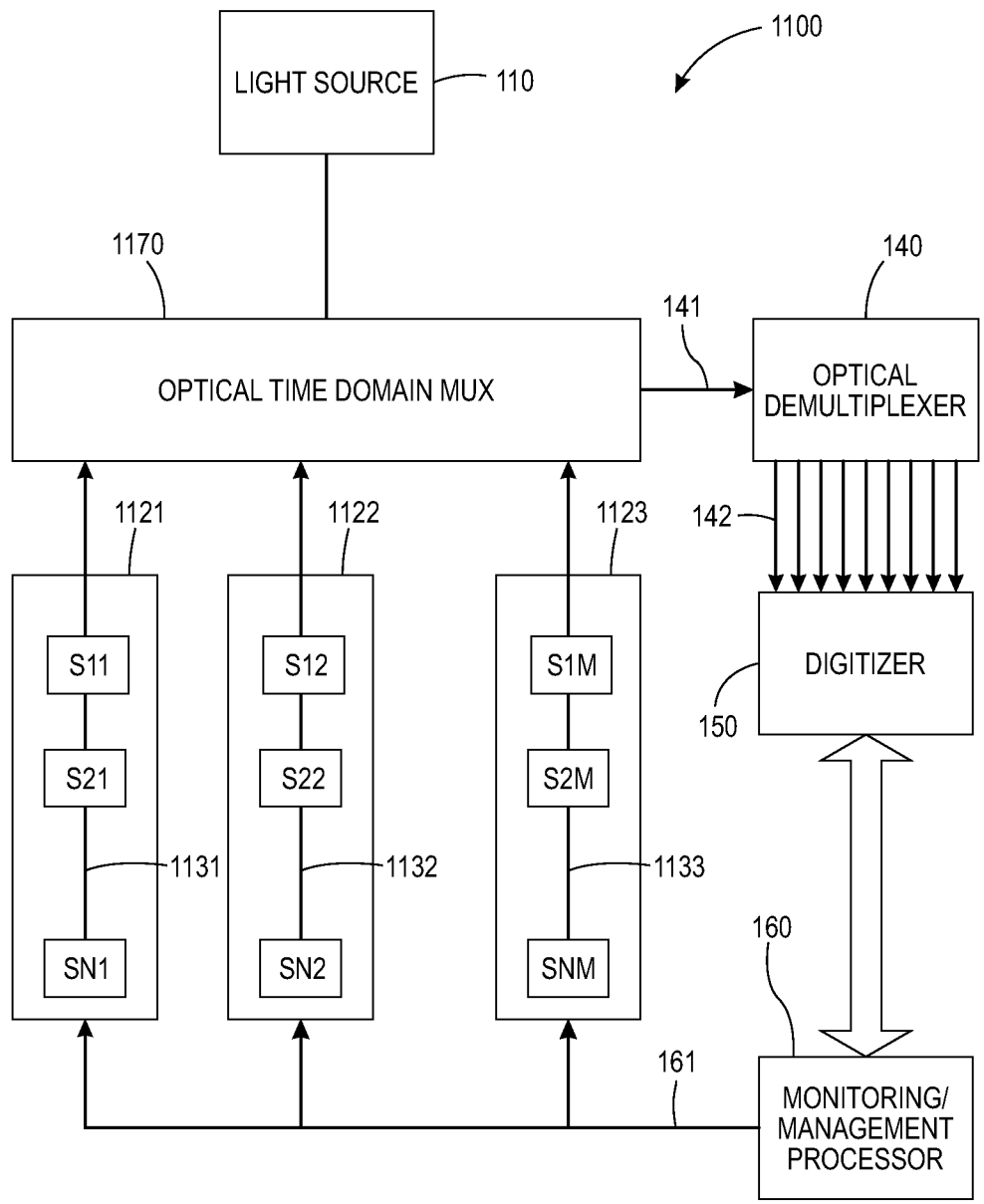
FIG. 11 is a block diagram of a monitoring system that includes both time and wavelength division multiplexing in accordance with some embodiments.

FIG. 11 shows a block diagram of a monitoring system 1100 that is similar in some respects to the monitoring system 100 of FIG. 1 and where like reference numbers indicate similar elements. System 1100 is capable of monitoring M modules 1121, 1122, . . . 1123, each module having N sensors. The optical outputs of the N sensors of each module 1121, 1122, . . . 1123 may be carried on a single optical fiber 1131, 1132, 1133 where the optical outputs of the sensors are distributed in wavelength according to the output channels of the optical demultiplexer. The modules and the optical fibers/sensors may be identically constructed.

Input light is passed from the light source 110 to the modules 1121, 1122, . . . 1123 through optical time domain mux 1170 and through waveguides 1131, 1132, . . . 1133, and interacts with the sensors S11 . . . SNM. Output light from the modules 1121, 1122, . . . 1123 is passed to the optical wavelength domain demultiplexer 140 through the optical time domain multiplexer 1170. The modules 1121, 1122, . . . 1123 are selected one at a time by the optical time domain multiplexer 1170. Implementations that combine time domain multiplexing and wavelength domain multiplexing and demultiplexing of sensor output light as disclosed herein are able to address a far greater number of battery cells (or other energy system components) than could be addressed by either time domain multiplexing or wavelength domain multiplexing/demultiplexing alone.

Figure 12:
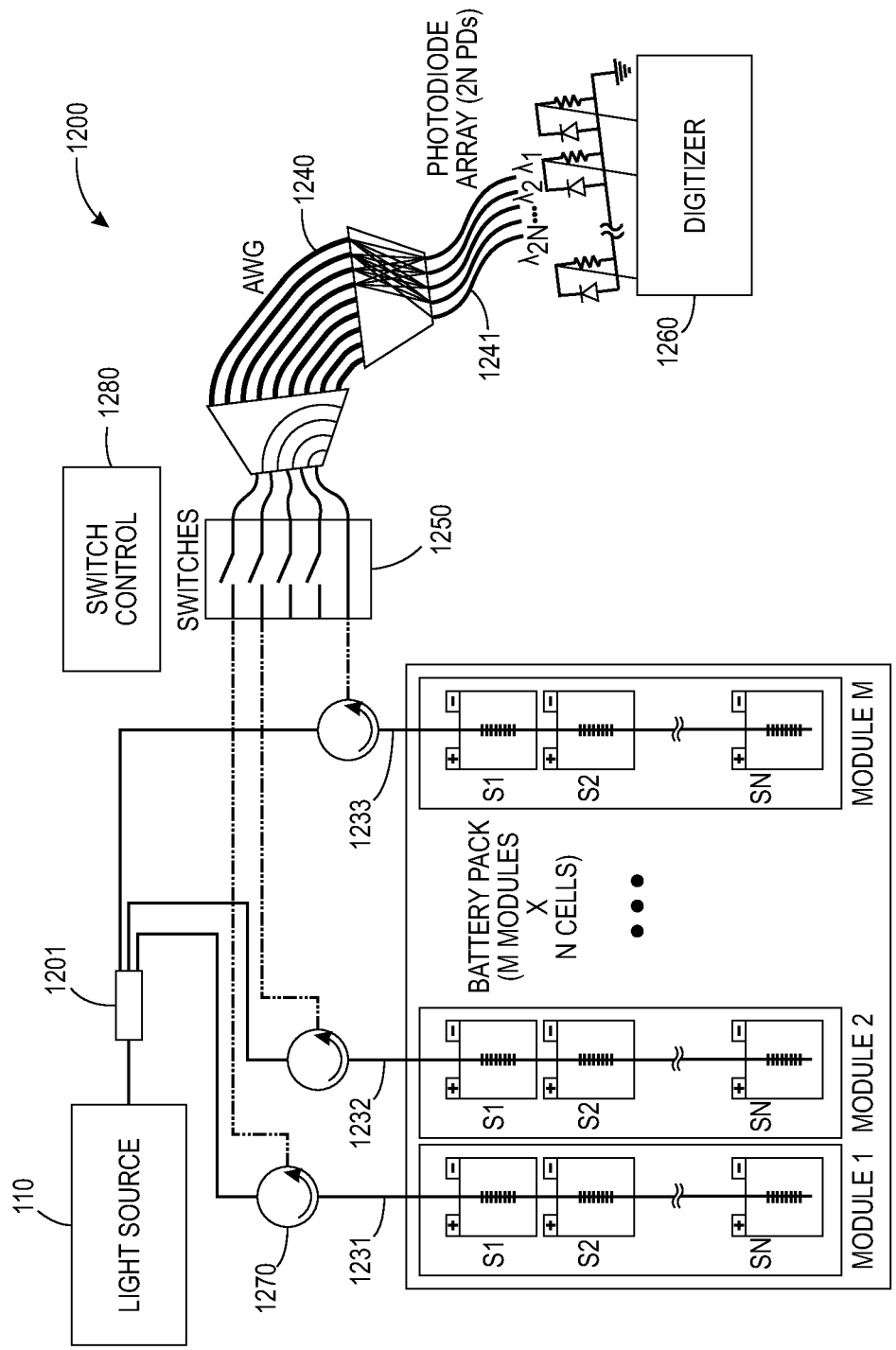
FIG. 12 shows a block diagram of a monitoring system that implements a bank of M optical switches for time division multiplexing and an AWG for wavelength division multiplexing in accordance with some embodiments.

FIG. 12 shows a configuration of a system 1200 that uses both time domain multiplexing and wavelength domain multiplexing to address multiple modules having multiple FBG sensors. In this particular example, the system 1200 monitors a battery pack using M sensor modules, each module having N FBG sensors S1, S2, . . . SN disposed in battery cells on a single optical fiber. The N FBGs are distributed in wavelength according to the output channels of an AWG 1240 used as an optical wavelength domain demultiplexer. The modules and the optical fibers/FBGs may be all identically constructed. Light is passed from the light source 110 to the battery modules by way of a 1×M optical power splitter 1201 and M circulators 1270. Sensor output light from Modules 1, 2, . . . M is passed through a time domain optical multiplexer 1250 to M inputs of an M-input by 2N-output AWG 1240. The time domain multiplexer 1250 comprises a bank of M optical switches controlled by switch control circuitry 1280. The output waveguides 1231, 1232, . . . 1233 of the modules 1 to M are selected one at a time and are optically coupled to the respective input waveguide of the AWG 1240. The AWG 1240 spatially disperses the light from the sensor modules to the AWG output waveguides 1241 and then the output light is routed to digitizer 1260 as previously discussed.

Figure 13:
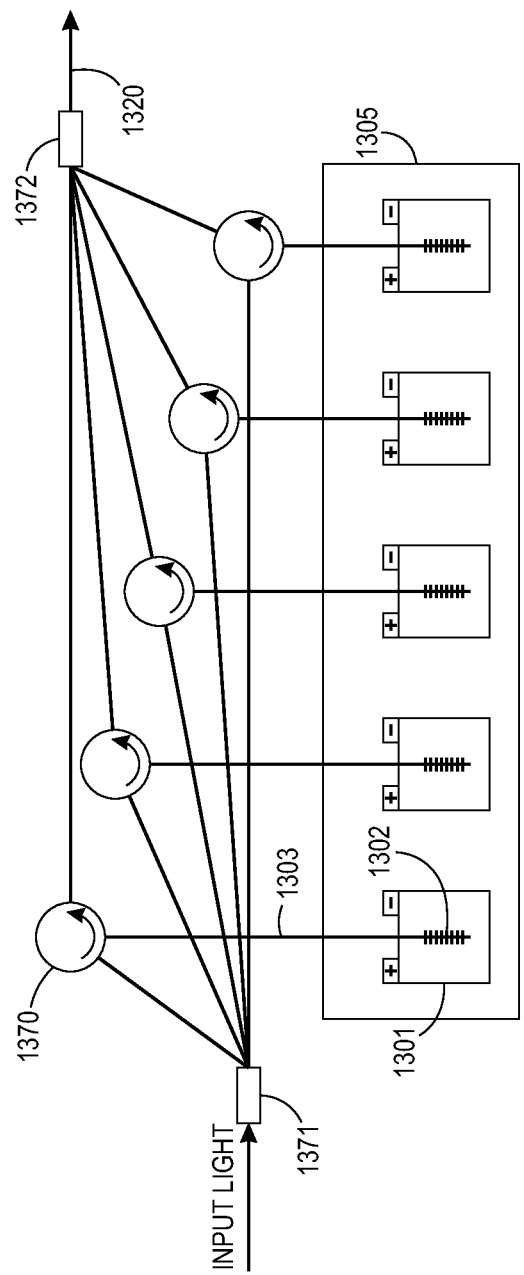
FIG. 13 illustrates a configuration for multiplexing sensor output light at the module level.

FIG. 12 depicts sensors S1, S2, . . . SN arranged so that the output light of each sensor is multiplexed onto the single output waveguide 1231, 1232, . . . 1233 for the module. FIG. 13 shows an alternative configuration for multiplexing sensor output light having different wavelength bands at the module level. In this configuration, each battery cell 1301 is monitored by one or more FBGs 1302 disposed on a sensor optical waveguide 1303. Input light is optically coupled through a 1×N power splitter 1371 to circulators 1370. The circulators 1370 connect the sensor output waveguides 1303 in parallel to through an N×1 power splitter 1372 to the output waveguide 1320 for the module 1305. The output waveguide carries the combined (wavelength multiplexed) output light from all FBGs 1302 in the module 1305. The module arrangement shown in FIG. 13 can be used to replace each of the modules shown in FIG. 8 or 12, for example.

Figure 14:
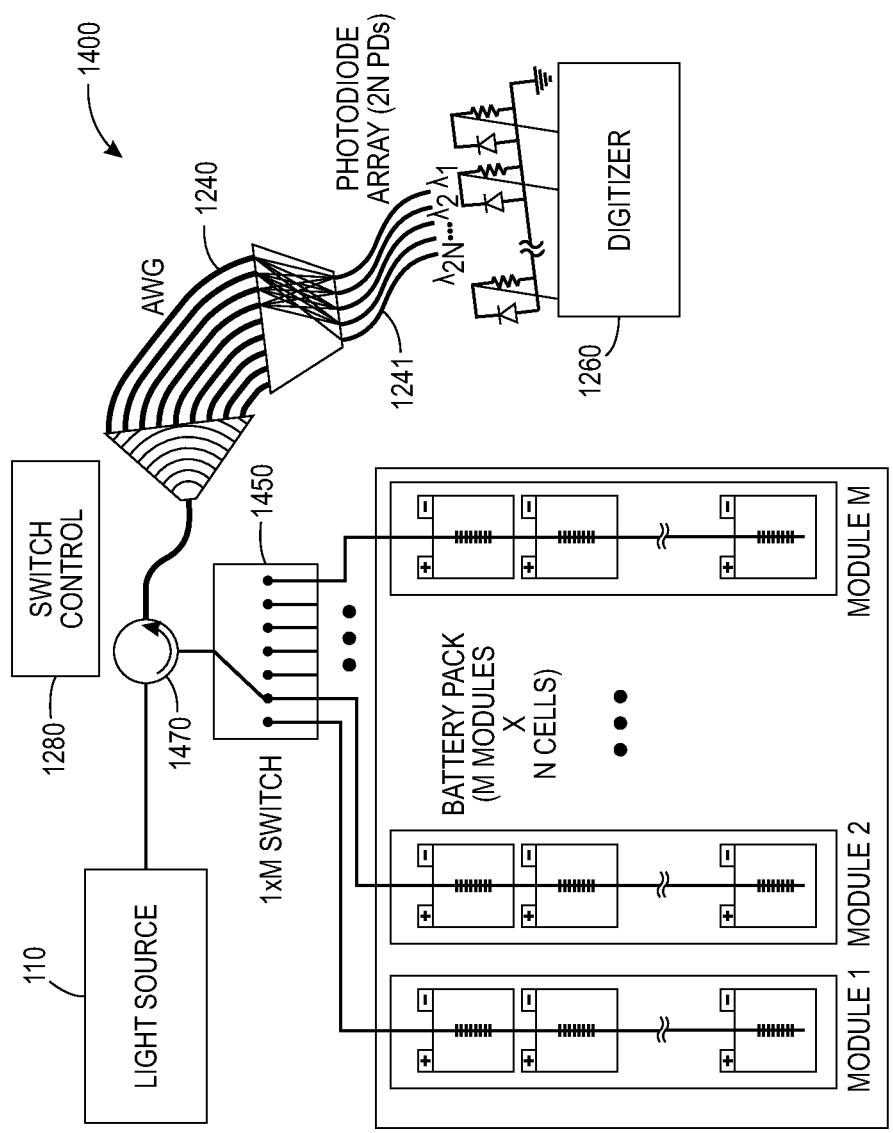
FIG. 14 depicts a monitoring system that uses time division multiplexing and wavelength division multiplexing in accordance with some embodiments.

FIG. 14 depicts another monitoring system 1400 that uses time domain multiplexing and wavelength domain multiplexing in accordance with some implementations. The monitoring system 1400 of FIG. 14 is similar in some respects to the monitoring system of 1200 and like reference numbers are used to refer to similar elements. System 1400 replaces the M optical switches 1250 and M optical circulators 1270 with a 1×M optical switch 1450 and an optical circulator 1470 disposed between the switch 1450 and light source 110.

Figure 15A:
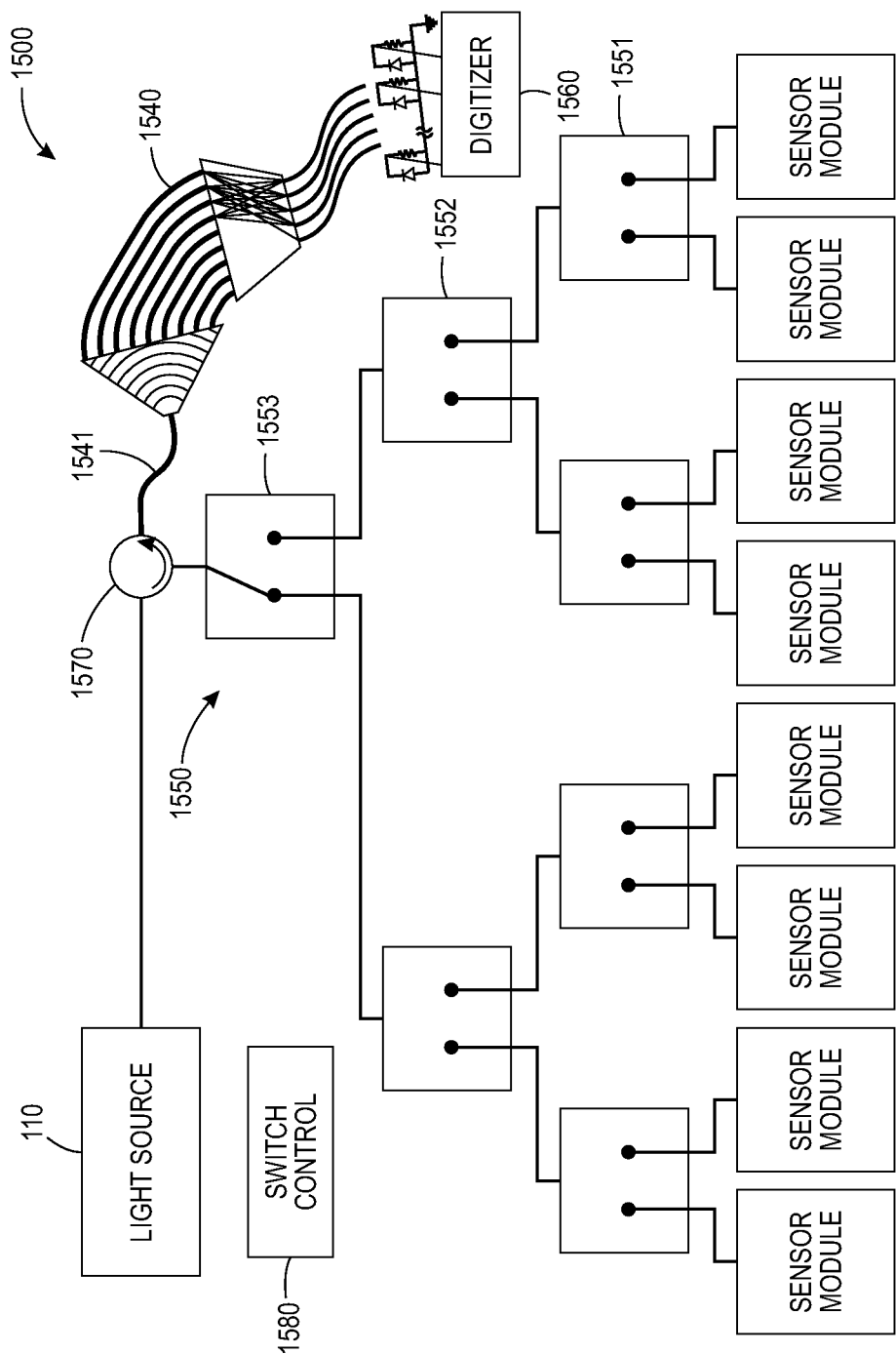
FIG. 15A is a block diagram illustrating a hierarchical switch arrangement that may be used for time division multiplexing.

FIG. 15A illustrates a monitoring system 1500 that includes a hierarchical switching arrangement to implement optical time domain multiplexing. The switching arrangement 1550 in the illustrated monitoring system 1500 includes a first level of four 1×2 optical switches 1551 (the bottom-most level of switches in FIG. 15A) coupled to 8 sensor modules, a second level of two 1×2 optical switches 1552 (the next to bottom-most level of switches in FIG. 15A) optically coupled between the first level switches 1551 and a single 1×2 third level optical switch 1553. The switching arrangement 1550 is connected to the light source 110 and the wavelength division demultiplexer (AWG) 1540 through an optical circulator 1570. The switches 1551, 1552, 1553 are controlled by switch control circuitry 1580 such that the output light from each sensor module is time multiplexed into the input waveguide 1541 of the AWG. The AWG 1540 demultiplexes the time multiplexed sensor output light, spatially dispersing the output light according to wavelength to the output waveguides and to the digitizer 1560.

Figure 15B:
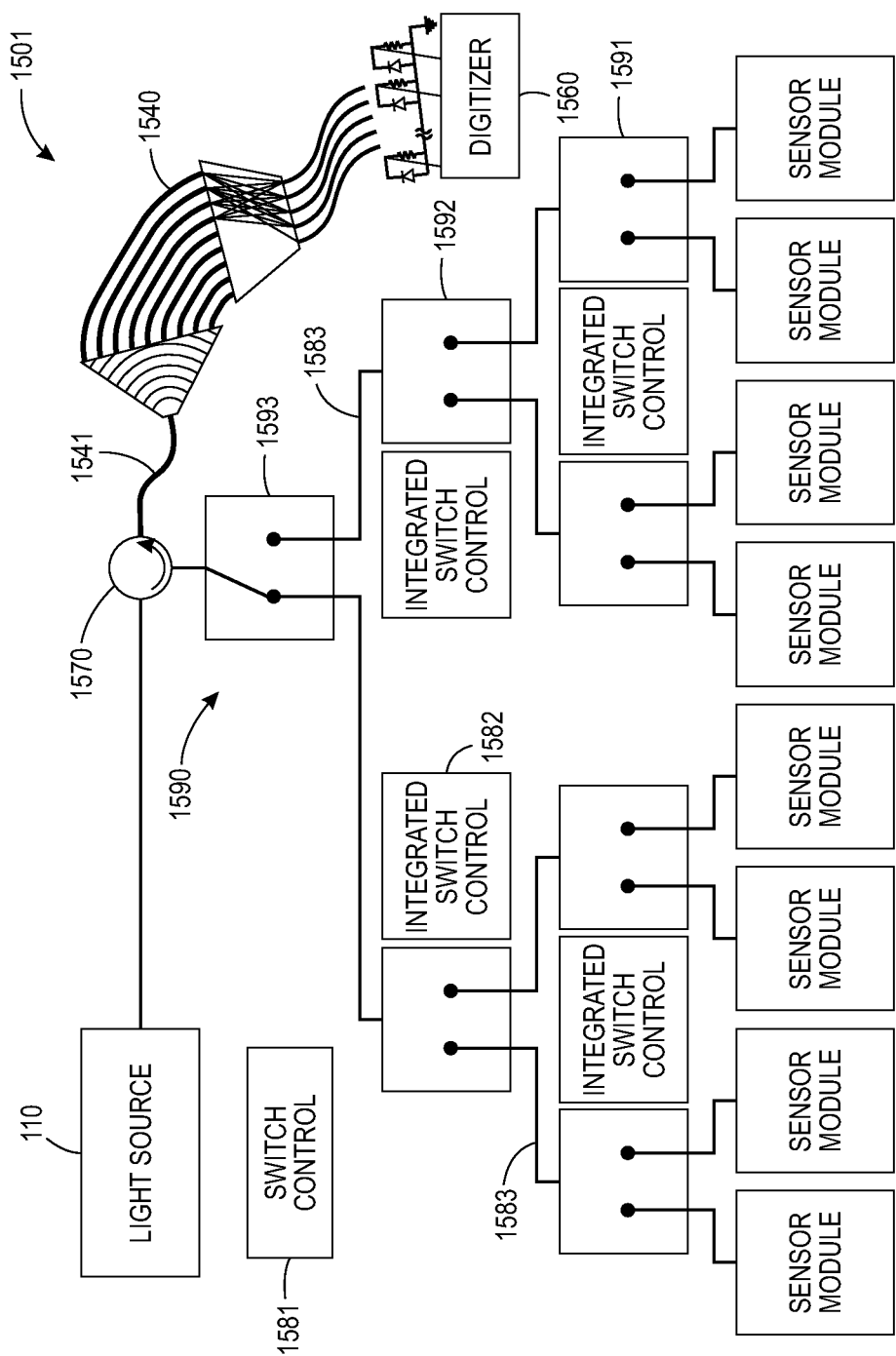
FIG. 15B is a block diagram illustrating a hierarchical switch arrangement with integrated switch control that may be used for time division multiplexing.

FIG. 15B illustrates a monitoring system 1501 that includes a hierarchical switching arrangement with integrated switch control to implement optical time division multiplexing. The switching arrangement 1590 in the illustrated monitoring system 1501 includes a first (bottom-most) level of four 1×2 optical switches 1591 coupled to 8 sensor modules, a second (next highest) level of two 1×2 optical switches 1592 optically coupled between the first level switches 1591 and the single 1×2 third level optical switch 1593. The switching arrangement 1590 is connected to the light source 110 and the wavelength division demultiplexer (AWG) 1540 through an optical circulator 1570. The switches 1591, 1592, 1593 are controlled by integrated switch control circuitry 1582 and optionally additionally by central switch control circuitry 1581 such that the output light from each sensor module is time multiplexed into the input waveguide 1541 of the AWG. The AWG 1540 demultiplexes the time multiplexed sensor output light, spatially dispersing the output light according to wavelength to the output waveguides and to the digitizer 1560.

The switch control circuitry 1581, 1582 operates to time multiplex output light from the sensor modules to the AWG 1540. In some implementations, at least one of the switches 1591, 1592, 1593 or groups of switches are associated with an integrated switch control element 1582. In some implementations, a control signal to change switch state is carried to an integrated switch control element 1582 from other integrated switch control elements or from the central switch control 1581 by the optical waveguides 1583 that optically couple the switches 1591, 1592, 1593. The integrated switch control may include electro-optical components or circuitry configured to receive an optical control signal, e.g., a digital signal, that includes a command to change switch state via the waveguide; to interpret the command; and to control the switch to change switch state.

In some embodiments, switch control to implement time division multiplexing may be performed by the integrated switch control elements in communication with each other. In these embodiments, the integrated switch control elements have the capability of receiving and interpreting commands to change switch state as well as sending commands to other integrated switch control elements. In some embodiments, the switch control may be implemented by the integrated switch control elements operating in conjunction with a central switch control.

A variety of types of optical switches can be used for the time division multiplexers discussed herein. Suitable optical switch technologies include micro-electro-mechanical systems (MEMS) optical switches, liquid crystal switches, bubble switches, thermo-optic switches, phased-array switches, and electro-holographic switches, for example.

Figure 16:
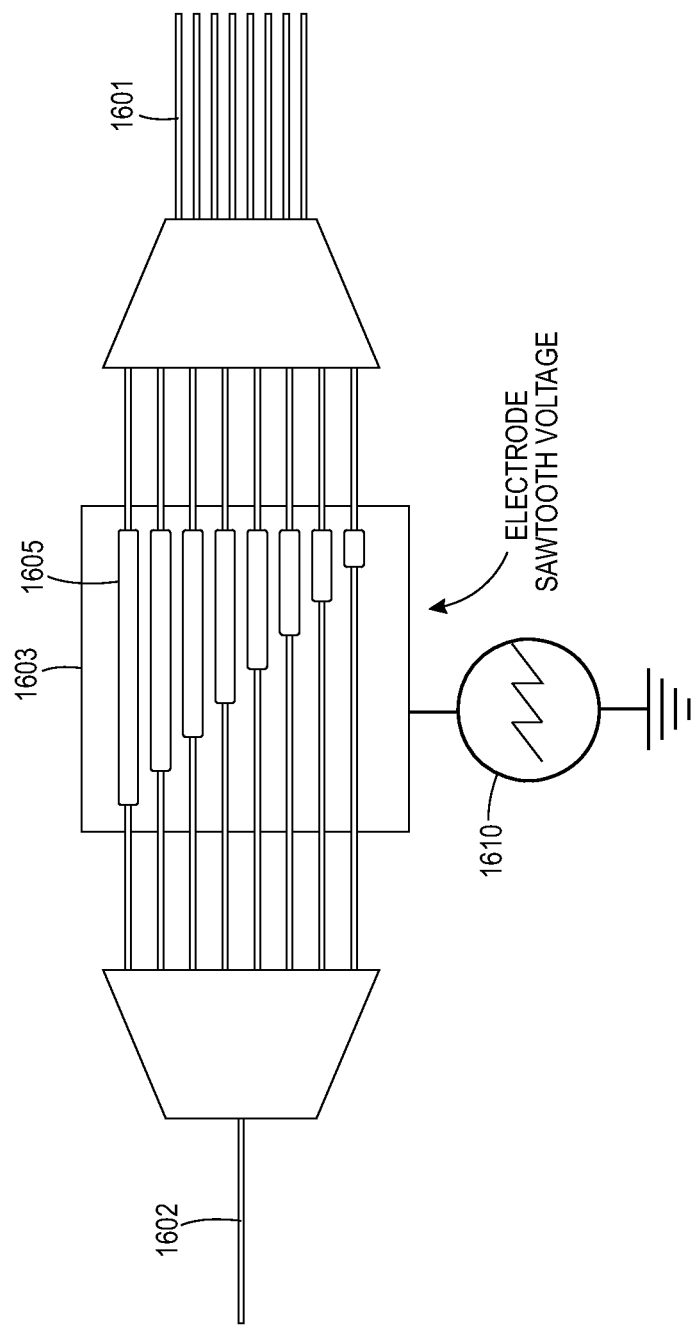
FIG. 16 depicts a 1×M multiplexing switch in accordance with some embodiments.

In some implementations, the optical time division multiplexer may be implemented by a 1×M phased array optical switch as illustrated in FIG. 16. In these implementations, the input optical signals carried on input waveguides 1601 are time multiplexed to an output waveguide 1602 by a voltage-controlled phase modulator section 1603 having a phase delay material 1605, such as $LiNbO_3$, of varying length along the input waveguides 1601. The voltage controlled phase modulator 1603 can be configured to induce phase modulation along the input waveguides 1601 in response to a time varying electrical signal 1610, such as the sawtooth wave shown. For example, the phase modulator material 1605 may have a linearly varying length along the input waveguides 1601 to provide a linearly varying phase modulation such that time multiplexing can be implemented by a linearly varying periodic electrical signal 1610. Other configurations for the phase delay switch are possible, including different waveforms, separate electrodes for each waveguide within the phase modulator section, identical length phase shifting sections, other phase shifting waveforms, silicon phase modulators based on free-carrier injection, etc.

The monitoring systems proposed herein may include one or more components that are integrated onto the same substrate. For example, it is possible to implement the monitoring system using discrete components, e.g., by fiber-coupling the outputs of the AWG and then sending the AWG output to individual fiber-coupled photodetectors.

Alternatively, the photodetectors, e.g., photodiodes, could be integrated directly into the output waveguides of the AWG. Integrating one or more of the monitoring system components onto the same substrate can yield substantial cost, size, and complexity savings. Note that it may be possible to integrate all components onto the same substrate, including the light source, circulator, optical switches, AWG, photodiodes, and digitizer, using electronic/photonic circuit hybrid integration methods.

The approaches discussed herein can provide a high degree of sensor multiplexing with a single detector portion as well as the potential for high levels of integration. Some or all components of the detector portion of the monitoring system—light source, circulator(s), time division multiplexer, wavelength division demultiplexer, and digitizer—could be integrated onto the same substrate, with the only external connections being electrical connections to a power source, electrical and/or optical communications with the monitoring and/or management processor, and optical fiber connections to the sensors. Such an integrated device could potentially yield significant cost/size/performance enhancements when manufactured in high volumes (e.g., automotive) as compared to non-integrated approaches. The proposed combination of time and wavelength-domain multiplexing for modular battery packs can enable pack monitoring with a compact, centralized readout. It helps retain the modular structure of the battery pack, facilitating the replacement or expansion of modules. It also simplifies the construction of the modules, since they can be made identical. A single fiber-optic cable can be used for each module, reducing cost and cabling. The wavelength coupling to the various output channels can be selected for sensing applications by deliberately introduced/designed cross-talk between adjacent channels. For automotive/electric vehicles, the single centralized readout can also be used to read out other optical fiber sensors distributed across the vehicle, especially in combination with the hierarchical network of time-domain multiplexers.

Different waveguide materials for the AWG would be used depending on the wavelengths of the optical sensors. For example, although silicon can be used at telecommunications wavelengths (around 1550 nm) it is not suitable for use in the visible wavelength range, which may be of more interest for chemical sensing approaches. In the visible wavelength range, silicon dioxide may be suitable as a waveguide material; in addition, silicon dioxide is also transparent at telecommunications wavelengths.

In some embodiments, rather than using a differential readout based on two photodetectors to determine the shifts in centroid wavelength, all 2N outputs of the AWG may be measured. An estimation routine may be employed using that information to simultaneously determine the centroids and peak intensities of up to N spectral peaks with known shape. For example, all spectral peaks may be fit simultaneously to all of the recorded information. There can be multiple FBGs or optical fiber sensors per battery cell (or other energy system component), or only one; and, the sensors can be located inside and/or outside the battery cells. Any kind of sensor can be used as long as the information to be sensed can be encoded in a wavelength shift, and preferably, the sensors are amenable to some form of wavelength division multiplexing (e.g., they operate in substantially non-overlapping spectral bands).

Various combinations of time domain multiplexing and wavelength domain multiplexing/demultiplexing can be employed, with reduction in the overall cost and/or size and/or complexity of the entire system being a goal in some implementations. Other schemes for time multiplexing using multiple light sources fired sequentially in time can also potentially be employed. For example, light source A covering a spectral range A and light source B covering a substantially different spectral range B can be coupled onto the same optical fiber. Sensors can be placed along the fiber such that a portion of the sensors produce a response when excited in the spectral range A and another portion of the sensors produce a response when excited in the spectral range B. (It may be advantageous to choose the spectral ranges A and B to fall within different diffraction orders of the AWG, as the AWG has a cyclical response with respect to optical frequency). Therefore, by sequentially firing the two (or more) light sources, signals from the different sensor groups can be time-multiplexed onto the same optical fiber and/or detector.

In some embodiments, the AWG channel wavelengths can be tuned in situ with a temperature controller, or athermalized AWGs (where the dependence on temperature of the channel center wavelengths has been reduced or minimized) can be used. It may still be useful to incorporate some facility to measure the temperature of the AWG and to include that information in any algorithm which calculates a wavelength shift from photodiode currents. In implementations that measure a wavelength shift from looking at the difference in light flux at the output of a pair of adjacent AWG waveguides, there is a tradeoff between the dynamic range with which the wavelength shift of a single spectral peak can be measured and the number of peaks that can be measured with a single AWG. For example, with a 100 channel AWG, one could measure the wavelength shifts of up to 50 spectral peaks (when the channels are observed pairwise), with a maximum range of the full bandwidth of the AWG divided by 100. By limiting the number of spectral peaks measured to 5, then each peak can be measured with the same resolution as before, but it can also be measured with 10× the range.

In some embodiments, the AWG may be used for pre-sorting of the different spectral peaks, and the wavelength shift of each spectral peak is then determined using a linearly varying transmission structure and photodetector array as described above. In this case, it may be useful to increase the pass-band of each AWG channel to accommodate the spectral shift of the sensor, e.g., such that the AWG dispersion accommodates the full range of expected spectral shift.

Systems, devices, or methods disclosed herein may include one or more of the features, structures, methods, or combinations thereof described herein. For example, a device or method may be implemented to include one or more of the features and/or processes described herein. It is intended that such device or method need not include all of the features and/or processes described herein, but may be implemented to include selected features and/or processes that provide useful structures and/or functionality.

In the above detailed description, numeric values and ranges are provided for various aspects of the implementations described. These values and ranges are to be treated as examples only, and are not intended to limit the scope of the claims. For example, embodiments described in this disclosure can be practiced throughout the disclosed numerical ranges. In addition, a number of materials are identified as suitable for various implementations. These materials are to be treated as exemplary, and are not intended to limit the scope of the claims.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. A monitoring system for an energy system, comprising:
N>1 optical sensors, each optical sensor operating within a different wavelength range and emanating output light in response to input light, the output light having a centroid wavelength that changes in response to a sensed parameter of the energy system;
a plurality of photodetectors, each photodetector configured to generate an electrical signal in response to light incident on a light sensitive surface of the photodetector; and
an optical coupler including at least one input waveguide configured to receive light from the optical sensors and a plurality of output waveguides, the optical coupler configured to disperse light from the input waveguide to the output waveguides according to wavelength of light so that sensor output light emanating from each optical sensor is optically coupled through at least one output waveguide to at least one photodetector, wherein the electrical signal generated by the photodetector in response to the sensor output light provides information about the sensed parameter of the energy system, wherein:
the plurality of output waveguides comprises N pairs of output waveguides;
the plurality of photodetectors comprises N pairs of photodetectors; and
the optical coupler is configured to spatially disperse light from the input waveguide according to wavelength so that the output light emanating from each optical sensor is optically coupled to a pair of photodetectors through a pair of adjacent output waveguides and the output waveguides in the pair are arranged and configured to allow crosstalk between the pair of output waveguides.

2. The system of claim 1, wherein the optical coupler comprises an arrayed waveguide grating.

3. The system of claim 1, wherein the optical coupler comprises a linear variable filter.

4. The system of claim 1, wherein the N pairs of output waveguides are configured so that the crosstalk between the output waveguides of the pair of output waveguides is greater than crosstalk between either of the output waveguides of the pair and a waveguide of an adjacent pair.

5. The system of claim 1, further comprising at least one additional optically dispersive element between the optical coupler and the photodetectors.

6. The system of claim 1, wherein the optical coupler comprises an arrayed waveguide grating having at least N output waveguides, each output waveguide having a wavelength pass-band at least equal to a range of an expected spectral shift of output light of an associated optical sensor.

7. The system of claim 1, further comprising processor circuitry configured to perform an estimation routine using the electrical signals to locate centroids of output light emanating from the N sensors.

8. The system of claim 1, wherein the N optical sensors are arranged along a single sensor waveguide.

9. The system of claim 1, wherein the energy device is a battery.

10. The system of claim 1, wherein the photodetectors and optical coupler are arranged on a wafer as an integrated electro-optical subsystem.

11. The system of claim 1, wherein the N optical sensors are disposed on multiple sensor waveguides, and further comprising an optical multiplexer optically coupled between the multiple sensor waveguides and the input waveguide.

12. The system of claim 1, wherein the output waveguides are adjacent and a center-to-center spacing between the adjacent output waveguides in the pair of output waveguides is on the order of a full width half maximum intensity (FWHM) optical spot size at an input of the output waveguides.

13. The system of claim 11, wherein the optical multiplexer comprises a wavelength division multiplexer.

14. The system of claim 12, wherein the spacing is between about ⅕ and about 5 times the FWHM optical spot size at the input of the output waveguides.

15. The system of claim 12, wherein the spacing is between about ½ and about 2 times the FWHM optical spot size at the input of the output waveguides.

16. A monitoring system for an energy system, comprising:
N>1 optical sensors, each optical sensor operating within a different wavelength range and emanating output light in response to input light, the output light having a centroid wavelength that changes in response to a sensed parameter of the energy system;
a plurality of photodetectors, each photodetector configured to generate an electrical signal in response to light incident on a light sensitive surface of the photodetector; and
an optical coupler including at least one input waveguide configured to receive light from the optical sensors and a plurality of output waveguides, the optical coupler configured to disperse light from the input waveguide to the output waveguides according to wavelength of light so that sensor output light emanating from each optical sensor is optically coupled through at least one output waveguide to at least one photodetector, wherein the electrical signal generated by the photodetector in response to the sensor output light provides information about the sensed parameter of the energy system,
wherein the optical coupler comprises an arrayed waveguide grating including K array waveguides optically coupled to the input waveguide, wherein K is chosen according to the formula $$\frac{\lambda}{m\Delta\lambda} \leq K \leq \frac{4\lambda}{m\Delta\lambda},$$

$\Delta\lambda$ is an expected operational range of the sensor with a center wavelength $\lambda$, and m is a diffraction order of the AWG.

17. A monitoring system for an energy system, comprising:
N>1 optical sensors, each optical sensor operating within a different wavelength range and emanating output light in response to input light, the output light having a centroid wavelength that changes in response to a sensed parameter of the energy system;
a plurality of photodetectors, each photodetector configured to generate an electrical signal in response to light incident on a light sensitive surface of the photodetector; and
an optical coupler including at least one input waveguide configured to receive light from the optical sensors and a plurality of output waveguides, the optical coupler configured to disperse light from the input waveguide to the output waveguides according to wavelength of light so that sensor output light emanating from each optical sensor is optically coupled through at least one output waveguide to at least one photodetector, wherein the electrical signal generated by the photodetector in response to the sensor output light provides information about the sensed parameter of the energy system, wherein the optical coupler comprises an arrayed waveguide grating including K array waveguides optically coupled to the input waveguide, the K array waveguides spaced a distance d apart, each array waveguide arranged a distance f from an input of an output waveguide, wherein a spacing between a pair of adjacent output waveguides is less than $2f\lambda/Kd$.

18. A monitoring system for an energy system, comprising:

N>1 optical sensors, each optical sensor operating within a different wavelength range and emanating output light in response to input light, the output light having a centroid wavelength that changes in response to a sensed parameter of the energy system;

a plurality of photodetectors, each photodetector configured to generate an electrical signal in response to light incident on a light sensitive surface of the photodetector; and an optical coupler including at least one input waveguide configured to receive light from the optical sensors and a plurality of output waveguides, the optical coupler configured to disperse light from the input waveguide to the output waveguides according to wavelength of light so that sensor output light emanating from each optical sensor is optically coupled through at least one output waveguide to at least one photodetector, wherein the electrical signal generated by the photodetector in response to the sensor output light provides information about the sensed parameter of the energy system, wherein the optical coupler comprises an arrayed waveguide grating including K array waveguides optically coupled to the input waveguide and wherein inputs of the output waveguides are positioned away from focal points of the array waveguides.

19. A monitoring system for an energy system, comprising:

N>1 optical sensors, each optical sensor operating within a different wavelength range and emanating output light in response to input light, the output light having a centroid wavelength that changes in response to a sensed parameter of the energy system;

a plurality of photodetectors, each photodetector configured to generate an electrical signal in response to light incident on a light sensitive surface of the photodetector; and an optical coupler including at least one input waveguide configured to receive light from the optical sensors and a plurality of output waveguides, the optical coupler configured to disperse light from the input waveguide to the output waveguides according to wavelength of light so that sensor output light emanating from each optical sensor is optically coupled through at least one output waveguide to at least one photodetector, wherein the electrical signal generated by the photodetector in response to the sensor output light provides information about the sensed parameter of the energy system, wherein:
the photodetectors comprise 2N pairs of photodetectors, each photodetector pair including a first and a second photodetector, the first photodetector configured to generate a current, $I_1$, in response to light incident on the light sensitive surface of the first photodetector and a second photodetector configured to generate a current, $I_2$, in response to light incident on the light sensitive surface of the second photodetector, and wherein a change in the sensed parameter causes a change in a ratio between $I_1$ to $I_2$.

20. A monitoring system for an energy system, comprising:

N>1 optical sensors, each optical sensor operating within a different wavelength range and emanating output light in response to input light, the output light having a centroid wavelength that changes in response to a sensed parameter of the energy system;

a plurality of photodetectors, each photodetector configured to generate an electrical signal in response to light incident on a light sensitive surface of the photodetector; and an optical coupler including at least one input waveguide configured to receive light from the optical sensors and a plurality of output waveguides, the optical coupler configured to disperse light from the input waveguide to the output waveguides according to wavelength of light so that sensor output light emanating from each optical sensor is optically coupled through at least one output waveguide to at least one photodetector, wherein the electrical signal generated by the photodetector in response to the sensor output light provides information about the sensed parameter of the energy system, wherein the N optical sensors are disposed on multiple sensor waveguides, and further comprising an optical multiplexer optically coupled between the multiple sensor waveguides and the input waveguide; and wherein the optical multiplexer comprises a time division multiplexer, the time domain multiplexer comprising at least one of:

a set of M optical switches; and a single 1× M optical switch.

21. A monitoring system for an energy system, comprising:

N>1 optical sensors, each optical sensor operating within a different wavelength range and emanating output light in response to input light, the output light having a centroid wavelength that changes in response to a sensed parameter of the energy system;

a plurality of photodetectors, each photodetector configured to generate an electrical signal in response to light incident on a light sensitive surface of the photodetector; and an optical coupler including at least one input waveguide configured to receive light from the optical sensors and a plurality of output waveguides, the optical coupler configured to disperse light from the input waveguide to the output waveguides according to wavelength of light so that sensor output light emanating from each optical sensor is optically coupled through at least one output waveguide to at least one photodetector, wherein the electrical signal generated by the photodetector in response to the sensor output light provides information about the sensed parameter of the energy system, wherein the N optical sensors are disposed on N sensor waveguides, and further comprising N optical circulators, each of the N sensor waveguides respectively optically coupled to the input waveguide through one of the N optical circulators.

22. A monitoring system, comprising:

M optical monitoring modules, each optical monitoring module comprising N>1 optical sensors, each optical sensor emanating sensor output light having a centroid wavelength that changes in response to a sensed parameter;

a plurality of photodetectors, each photodetector configured to generate an electrical output signal in response to light incident on a light sensitive surface of the photodetector;

a time domain optical multiplexer; and a wavelength domain optical demultiplexer optically coupled to the plurality of photodetectors through the time domain optical multiplexer, the time domain optical multiplexer configured to time multiplex module output light from each of the monitoring modules to the wavelength domain demultiplexer, the wavelength domain demultiplexer configured to spatially disperse the module output light of a selected monitoring module according to wavelength so that sensor output light from each optical sensor of the selected monitoring module is optically coupled to at least one photodetector through at least one output waveguide, wherein electrical signals generated by the photodetectors in response to the sensor output light provide information about the sensed parameter.

23. The system of claim 22, further comprising:
a light source configured to provide input light to the optical sensors; and
M optical circulators, each optical circulator arranged to optically couple the light source to one of the monitoring modules.

24. The system of claim 22, wherein the time domain optical multiplexer comprises a set of M optical switches.

25. The system of claim 22, wherein the time domain optical multiplexer comprises a single 1× M optical switch.

26. The system of claim 22, wherein at least one of the monitoring modules comprises N sensors disposed on a single sensor waveguide.

27. The system of claim 22, wherein at least one of the monitoring modules comprises:
N optical sensors disposed on multiple sensor waveguides, and
further comprising a optical multiplexer optically coupled between the multiple sensor waveguides and the time domain optical multiplexer.

28. The system of claim 22, wherein each monitoring module comprises:
N optical sensors disposed on a sensor waveguide, wherein the sensor waveguides of the M monitoring modules are optically coupled by M optical circulators to the time domain multiplexer.

29. The system of claim 22, wherein the time domain multiplexer comprises a hierarchical network of optical switches.

30. The system of claim 22, wherein the time domain multiplexer comprises:
multiple optical switches, each optical switch switchable to two or more states and having a control line that controls switching between the states;
multiple integrated switch control elements, each integrated switch control element coupled to some but not all of the optical switches, the integrated switch control elements configured to activate the multiple optical switches to implement time domain multiplexing.

31. The system of claim 22, wherein the time domain optical multiplexer includes one or more of:
optical-electronic-optical switches;
micro-electro-mechanical system switches;
liquid crystal switches;
bubble switches;
phased-array switches; and
thermo-optic switches.

32. The system of claim 22, wherein the time domain multiplexer comprises:
one or more optical switches, each optical switch switchable between two or more states and having a control line that controls switching between the states;
switch control circuitry configured to control the optical switches to implement time multiplexing of the module output light from each of the monitoring modules.

33. The system of claim 32, wherein the switch control circuitry comprises central switch control circuitry coupled to the optical switches and configured to change the states of the optical switches to implement the time multiplexing.

34. The system of claim 32, wherein the switch control circuitry comprises integrated local switch control circuitry associated with each optical switch and configured to receive commands and, based on the commands, to activate the optical switch to change the state of the optical switch to implement the time multiplexing.

35. The system of claim 34, wherein the commands are conveyed from a central switch control circuitry to the integrated local switch control circuitry as optical signals carried on an optical waveguide coupled to the optical switch.

36. A method comprising:
optically sensing multiple parameters of an energy system using N>1 optical sensors and generating multiple component optical signals, each component signal associated with a different wavelength range and having a centroid wavelength that changes in response to a sensed parameter of the system;
combining the component optical signals into a combined optical signal;
spatially dispersing the component optical signals of the combined optical signal according to wavelength so that output light emanating from each optical sensor is coupled to a pair of photodetectors through a pair of adjacent output waveguides, the output waveguides in the pair are arranged and configured to allow crosstalk between the pair of output waveguides; and
generating an electrical signal in response to each spatially dispersed component optical signal, the electrical signal including information about the sensed parameter of the energy system.

37. A method, comprising:
for each of M optical monitoring modules:
optically sensing multiple parameters of a system and generating multiple component optical signals, each component signal associated with a different wavelength range and having a centroid wavelength that changes in response to a sensed parameter of the energy system; and
combining the component optical signals into a combined optical signal;
time multiplexing an optical coupling between each of the combined optical signals of the M optical monitoring modules and a wavelength demultiplexer;
wavelength demultiplexing each of the combined optical signals, the wavelength demultiplexing comprising spatially dispersing the component optical signals of the combined optical signal according to wavelength; and generating an electrical signal in response to each spatially dispersed component optical signal, the electrical signal including information about the sensed parameter of the system.

* * * * *